(12) United States Patent
Salud et al.

(10) Patent No.: US 12,148,524 B1
(45) Date of Patent: *Nov. 19, 2024

(54) APPARATUSES, SYSTEMS, AND METHODS FOR REDUCING RETURN OF PRESCRIPTIONS TO STOCK

(71) Applicant: WALGREEN CO., Deerfield, IL (US)

(72) Inventors: Lawrence Salud, Chicago, IL (US); Zhou Jiang, Princeton, NJ (US)

(73) Assignee: WALGREEN CO., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/135,005

(22) Filed: Apr. 14, 2023

Related U.S. Application Data

(63) Continuation of application No. 16/871,224, filed on May 11, 2020, now Pat. No. 11,664,120.

(51) Int. Cl.
| | |
|---|---|
| *G16H 40/20* | (2018.01) |
| *G06Q 10/087* | (2023.01) |
| *G06Q 10/10* | (2023.01) |
| *G16H 10/60* | (2018.01) |
| *G16H 70/40* | (2018.01) |

(52) U.S. Cl.
CPC ........... *G16H 40/20* (2018.01); *G06Q 10/087* (2013.01); *G06Q 10/10* (2013.01); *G16H 10/60* (2018.01); *G16H 70/40* (2018.01)

(58) Field of Classification Search
CPC ........ G16H 40/20; G16H 10/60; G16H 70/40; G06Q 10/087; G06Q 10/10
See application file for complete search history.

(56) References Cited

U.S. PATENT DOCUMENTS

| | | | | |
|---|---|---|---|---|
| 5,745,366 A | * | 4/1998 | Higham | G07F 17/0092 700/242 |
| 2003/0204480 A1 | * | 10/2003 | Heinrichs | G06Q 10/087 |

(Continued)

OTHER PUBLICATIONS

Kumar, Dinesh, and D. Kumar. "Managing the Essential Medicines Stock at Rural Healthcare Systems in India." International journal of health care quality assurance 31.8 (2018): 950-65. (Year: 2018).*

(Continued)

*Primary Examiner* — Amber A Misiaszek

(74) *Attorney, Agent, or Firm* — MARSHALL, GERSTEIN & BORUN LLP; Randall G. Rueth

(57) ABSTRACT

Apparatuses, systems, and methods are provided for reducing return of prescriptions to stock. The apparatuses, systems and methods provide for one or more processors to: (1) store pharmacy prescription information in a standardized pharmacy format; (2) receive updated information in a non-standardized electronic prescription format for a prescription of a patient; (3) receive patient health record data; (4) generate prescription return to stock prediction data that indicates a probability the prescription of the patient would be returned to stock based upon the electronic prescription data, the patient health record data, and a predictive model; (5) convert the electronic prescription data and the prescription return to stock prediction data to pharmacy prescription information; and (6) generate a pharmacy prescription in a standardized format based on the updated pharmacy prescription information.

20 Claims, 12 Drawing Sheets

(56) References Cited

U.S. PATENT DOCUMENTS

| | | | | |
|---|---|---|---|---|
| 2006/0224414 A1* | 10/2006 | Astrup | ............... | G16H 10/60 |
| | | | | 705/2 |
| 2009/0287350 A1* | 11/2009 | Johnson | ............... | G07F 11/44 |
| | | | | 715/702 |
| 2013/0138577 A1* | 5/2013 | Sisk | ............... | G06Q 40/04 |
| | | | | 705/36 R |
| 2014/0114470 A1* | 4/2014 | Rashid | ............... | G16H 20/13 |
| | | | | 700/235 |

OTHER PUBLICATIONS

Levy, Sandra. "Supermarkets Stay Ahead." Drug Store News 42.5 (2020): 52-61. ProQuest (Year: 2020).

* cited by examiner

300

Medication: Prozac-capsules

Hx  Current: 12/10/2013 Prozac 10mg ▼ —328

Date: 12/10/2013 ▼   30 ▲▼ Days

324— Facility:   Prescriber: John Doe —316
  DEA#: AA55555555 —318
  License#: 111111111 —320
  Phone: —322

302— Name: Chris Bryant [...]  Age: 21 —304

Address: 555 N.MichiganAve. Chicago, IL —308

Date: 12/10/2013

310— Prozac-capsules 10mg —330

312— SIG: Ingest 4 10 mg capsules, once a day

Electronic Prescription

314— DISP: 120 ▲▼ Days

This Prescription will Be Filled Generically Unless DAW is Yes

326— DAW  No ▲▼

| Write | Print | Renew | Transmit |

Save    Cancel

*FIG. 3*

| Data Attribute | Data Attribute Business Description | Comments and Follow-ups |
|---|---|---|
| ACCEPT | accepted by insurance | |
| AUTO_PRE_IND | auto fill indicator prior yes or no | |
| AVG_RX_CNT_CY | store avg_rx_cnt | |
| AVG_SOLDGAP_PRE | avg_days between sold and enter date for sold rx in the prior 12m | Date when the prescription comes to Walgreens; Cohort is based on Enter Date; Create date is not used to define the cohort. |
| BRAND_MED | brand medication yes or no | |
| CASH | cash yes or no | |
| CENTRAL_CONTROL | reviewed by central yes or no -- who and why important? | |
| COMMERCIAL | commercial yes or no | indicator of large volume store |
| DELETE | delete y; return to stock, predictable; y is returned to stock. | Dependet Variable |
| DEMO_MISS_IND | missing demographic information indication | |
| DENTAL | dental yes or no | |
| DERMATOLOGIST | dermatologist yes or no | |
| DRUG_MISS_IND | drug missing indication | |
| DSPN_FILL_NBR | dispense filled indication | |
| EMAIL_IND | email avalable indication | |
| ER | er yes or no | Specialty/Which practice the perscription came from |
| ESCRIPT_IND | erx yes or no | |
| EYE_NOSE | eye_nose yes or no | |
| FEMALE | female yes or no | |
| FILL_DAYS_SUPPLY | fill days_supply | |
| FILL_ENTER_DT | fill enter date | |
| FILL_LABEL_PRICE_DLRS | out of pocket $ | This is the price that the patient pays. Could be copay. |
| GPI04 | gpi04 "*tetracyclines*" | |
| GPI05 | gpi05 *fluoroquinolones* | |

Fig. 4A

| Data Attribute | Data Attribute Business Description | Comments and Follow-ups |
|---|---|---|
| GPI10 | gpi10 '*penicillins*' | |
| GPI11 | gpi11 '*antifungals*' | |
| GPI12 | gpi12 '*antivirals*' | |
| GPI16 | gpi16 '*anti-infective agents - misc.*' | |
| GPI17 | gpi17 '*vaccines*' | |
| GPI20 | gpi20 '*cephalosporins*' | |
| GPI22 | gpi22 '*corticosteroids*' | |
| GPI25 | gpi25 '*contraceptives*' | |
| GPI27 | gpi27 '*antidiabetics*' | |
| GPI30 | gpi30 '*macrolides*' | |
| GPI33 | gpi33 '*beta blockers*' | |
| GPI34 | gpi34 '*calcium channel blockers*' | |
| GPI36 | gpi36 '*antihypertensives*' | |
| GPI37 | gpi37 '*diuretics*' | |
| GPI39 | gpi39 '*antihyperlipidemics*' | |
| GPI41 | gpi41 '*antihistamines*' | |
| GPI42 | gpi42 '*nasal agents - systemic and topical*' | |
| GPI43 | gpi43 '*cough/cold/allergy*' | |
| GPI44 | gpi44 '*antiasthmatic and bronchodilator agents*' | |
| GPI46 | gpi46 '*laxatives*' | |
| GPI49 | gpi49 '*ulcer drugs*' | |
| GPI50 | gpi50 '*antiemetics*' | |
| GPI53 | gpi53 '*urinary anti-infectives*' | |
| GPI56 | gpi56 '*genitourinary agents - miscellaneous*' | |
| GPI57 | gpi57 '*antianxiety agents*' | |
| GPI58 | gpi58 '*antidepressants*' | |

Fig. 4B

| Data Attribute | Data Attribute Business Description | Comments and Follow-ups |
|---|---|---|
| GPI61 | gpi61 "*adhd/anti-narcolepsy/anti-obesity/anorexiants*" | |
| GPI65 | gpi65 "*analgesics - opioid*" | |
| GPI66 | gpi66 "*analgesics - anti-inflammatory*" | |
| GPI72 | gpi72 "*anticonvulsants*" | |
| GPI75 | gpi75 "*musculoskeletal therapy agents*" | |
| GPI86 | gpi86 "*ophthalmic agents*" | |
| GPI88 | gpi88 "*mouth/throat/dental agents*" | |
| GPI90 | gpi90 "*dermatologicals*" | |
| GPI97 | gpi97 "*medical devices and supplies*" | |
| INTERNAL | internal yes or no | |
| LOC_AREA_TYPE | loc_area_type (rural, urban, suburban) | Definitely not in EDW-GIS ; GIS_VW; GIS_NS (Tables in Oracle database-May be maintained by other IT group); This field comes from a table that has store information. |
| MAINT_MED | maint_med yes or no | |
| MEDIAN_H_INCOME | median_h_income(<30k, 30k-40k, 40k-60k, 60k-80k, 80k-100k,>100k | Derived from block group level from GIS data. It is more specific than zip-code level; Submit file online and IT sends fips code containing race; etc. FIPS code/Block level/Race/Etc. |
| MEDICAID | medicaid yes or no | |
| N_EPISODE_PRE | total filled rx count in the prior 12m | Total prescription filled (episode) in the prior twelve month. (counts both sold or deletes ) |
| N_RTS_PRE | total rts delete counts in the prior 12m | |
| N_SOLD_PRE | total sold count in the prior 12m | Measure of total count of sold prescriptions in previous 12 months |
| NURSE | nurse yes or no | Occupation of originating |
| OBGYN | obgyn yes or no | |
| OPEN_24 | store open 24 yes or no | |
| PARTD | medicare partd yes or no | |
| PAT_AGE | pat_age | |
| PAT_ID | patient_id | |
| PBR_AGE | pbr_age | |
| PBR_CLASS | pbr_class | |
| PBR_FEMALE | pbr_female | |
| PEDIATRIAN | pediatrian yes or no | |
| PHONE_IND | patient_ind | |

Fig. 4C

| Data Attribute | Data Attribute Business Description | Comments and Follow-ups |
|---|---|---|
| RECENCY | the days between most recent sold_date and the index date | Indexed - Date that triggered to the system= Same as enter date |
| RX_CNT | total rx count of the day - counts revd? | Counts of all medication received both filled and new. |
| RX_CREATE_DT | rx created data | |
| RX_DAW_IND | rx_daw_ind yes or no | |
| RX_FILL_NBR | patient nbr | |
| RX_MISS_IND | patient ind | |
| RX_NBR | patient nbr | |
| RX_OTC_ALT | rx_otc_alternative yes or no | |
| SPCLTY_DRUG_IND | spclty_drug_ind yes or no | |
| STAR | star meds or non-star meds | Not in EDW. HARR developed a Star drug list based on CMS document updating monthly. Flag Star meds vs non-Star meds based on this list. NDC drug list from CMS. GPI6 is the most broad. |
| STR_NBR | patient nbr | |
| SURGON | surgon yes or no | |
| TXT_MSG_IND | txt_msg_ind yes or no | |
| WAITER | waiter or non-waiter | |
| WEEK | patient week | |
| WEEKEND_IND | weekend yes or no | |

Fig. 4D

APPARATUSES, SYSTEMS, AND METHODS FOR REDUCING RETURN OF PRESCRIPTIONS TO STOCK

CROSS-REFERENCE TO RELATED APPLICATION

This application is a continuation of U.S. patent application Ser. No. 16/871,224, entitled APPARATUSES, SYSTEMS, AND METHODS FOR REDUCING RETURN OF PRESCRIPTIONS TO STOCK, filed May 11, 2020, the entire disclosure of which is hereby expressly incorporated herein by reference.

TECHNICAL FIELD

The present disclosure generally relates to reducing return of prescriptions to stock. More particularly, the present disclosure relates to apparatuses, systems, and methods for reducing return of prescriptions to stock using a predictive model.

BACKGROUND

Each year millions of healthcare patients receive a prescription for medications and/or medical devices. Often times, a healthcare patient may not actually pick-up the medication and/or medical device.

Known prescription processing methods result in a prescription being filled whether or not an associated healthcare patient will actually pick-up a related medication or medical device. If the healthcare patient does not ultimately pick-up the related medication or medical device, the medication and/or medical device has to be returned to stock. Return of medications and/or medical devices to stock is expensive, time consuming, and introduces risk of error.

What is needed is a predictive model that may predict whether a healthcare patient will actually pick-up a medication and/or medical device that is associated with a prescription. Related apparatuses, systems and methods for reducing return of prescriptions to stock are also needed.

SUMMARY

An apparatus for reducing return of prescriptions to stock is provided. The apparatus includes one or more processors and a non-transitory computer-readable medium having computer-readable instructions stored thereon that, when executed by the one or more processors, cause the one or more processors to: (1) store pharmacy prescription information in a standardized pharmacy format about a prescription of a patient; (2) receive updated information in a non-standardized electronic prescription format dependent on the hardware and software platform used by the one or more users, wherein the electronic prescription data is representative of a prescription for a patient; (3) receive patient health record data in response to the one or more processors receiving the electronic prescription data; (4) generate prescription return to stock prediction data based upon the electronic prescription data, the patient health record data, and a predictive model, wherein the prescription return to stock prediction data is indicative of a probability of whether the prescription for the patient would be returned to stock; (5) convert, by the one or more processors, the electronic prescription data and the prescription return to stock prediction data to pharmacy prescription information; (6) generate a pharmacy prescription in a standardized format based on the updated pharmacy prescription information.

In another embodiment, a computer-readable medium having computer-readable instructions stored thereon that, when executed by a processor, may cause the processor to: (1) store pharmacy prescription information in a standardized pharmacy format about a prescription of a patient; (2) receive updated information in a non-standardized electronic prescription format dependent on the hardware and software platform used by the one or more users, wherein the electronic prescription data is representative of a prescription for a patient; (3) receive patient health record data in response to the one or more processors receiving the electronic prescription data; (4) generate prescription return to stock prediction data based upon the electronic prescription data, the patient health record data, and a predictive model, wherein the prescription return to stock prediction data is indicative of a probability of whether the prescription for the patient would be returned to stock; (5) convert, by the one or more processors, the electronic prescription data and the prescription return to stock prediction data to pharmacy prescription information; and (6) generate a pharmacy prescription in a standardized format based on the updated pharmacy prescription information.

In a further embodiment, a computer-implemented method to generate a predictive model for predicting return of prescriptions to stock is provided. The method may include (1) storing pharmacy prescription information in a standardized pharmacy format about a prescription of a patient; (2) receiving updated information in a non-standardized electronic prescription format dependent on the hardware and software platform used by the one or more users, wherein the electronic prescription data is representative of a prescription for a patient; (3) receiving prescription return to stock data, at the one or more processors, in response to the one or more processors executing a prescription return to stock data receiving module and further in response to the one or more processors receiving the electronic prescription data, wherein the prescription return to stock data is representative of at least one prescription that was known to have not been acquired by a patient; (4) generating, using the one or more processors, a predictive model, based on the prescription data and the prescription return to stock data, in response to the one or more processors executing a predictive model generation module; (5) converting, using the one or more processors, the electronic prescription data and the prescription return to stock prediction data to pharmacy prescription information; and (6) generating a pharmacy prescription in a standardized format based on the updated pharmacy prescription information.

BRIEF DESCRIPTION OF THE DRAWINGS

The figures described below depict various aspects of the system and methods disclosed therein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 3 depicts an exemplary electronic prescription (eRx) displayed on a display of a user device;

FIGS. 4A-D depict an example data structure for use in generating a predictive model for reducing return of prescriptions to stock;

DETAILED DESCRIPTION

Figure 1:
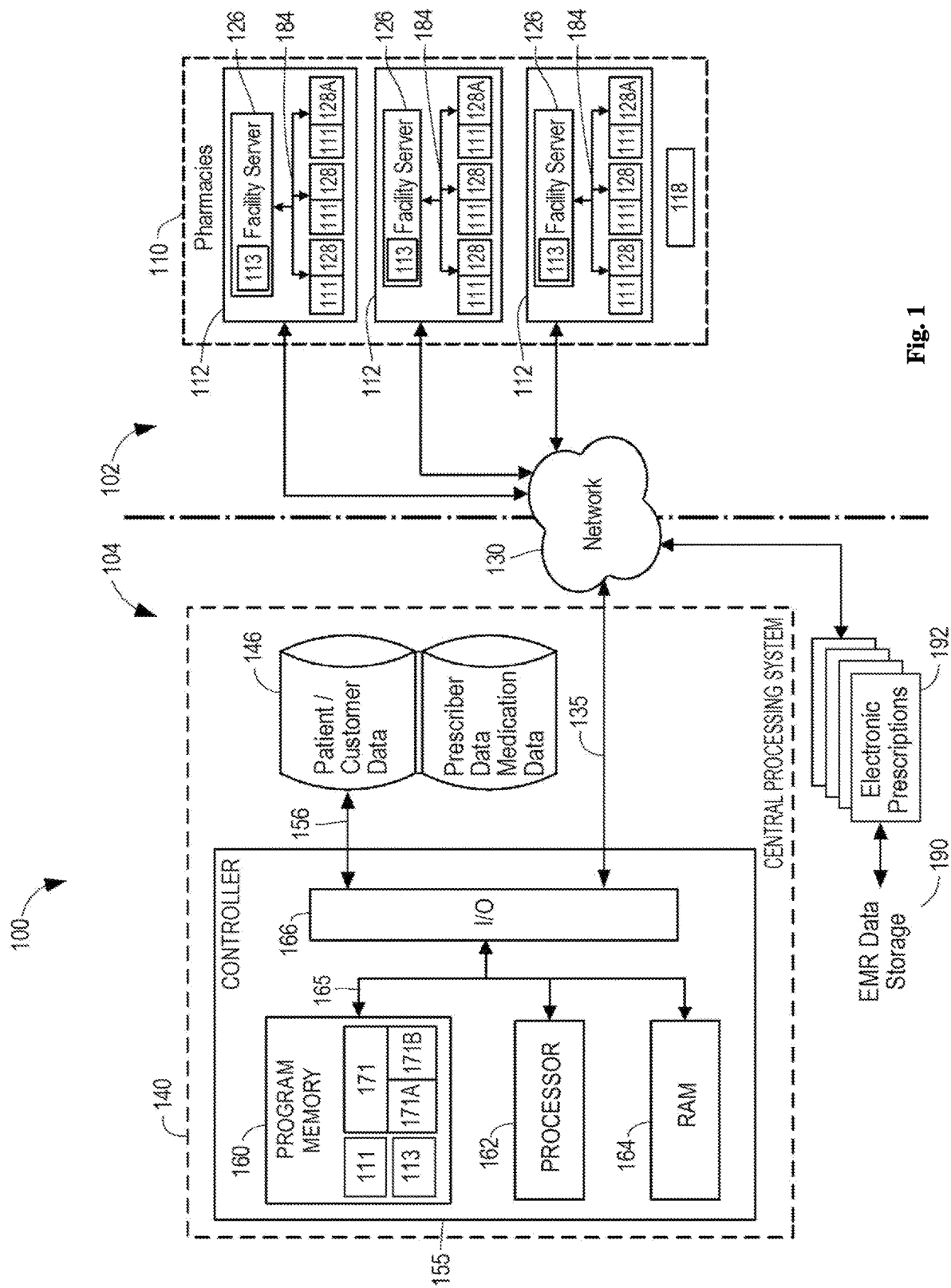
FIG. 1 depicts a block diagram of an exemplary computer system architecture for implementing a prescription processing system.

Apparatuses, systems, and methods are provided to reduce return of prescriptions to stock. The apparatuses, systems, and methods may reduce return of prescriptions to stock based on a predictive model. The predictive model may be based on data representative of a plurality of prescriptions and/or patient health records that have been previously correlated with data representative of whether a patient actually picked up a medication or medical device associated with a prescription. The apparatuses, systems, and methods may reduce return of prescriptions to stock based on a response of a patient to a notification that a prescription has been received for the patient.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

A "health care organization," as used herein, refers to a health care related enterprise or health care provider. The health care organization may be for profit or not-for-profit. The health care organization may provide health care diagnostic, therapeutic, rehabilitation, and other services to patients. For example, the health care organization may provide physician care, therapy, imaging, counseling, or the like. The health care organization may provide inpatient and/or outpatient services, may include one or more physical locations or facilities. Additionally or alternatively, the health care organization may provide other health-care related services, such as providing billing management, providing health care insurance, maintaining electronic medical records, etc. Examples of health care organizations may include a hospital group, a medical practice group, an insurance group, a stand-alone imaging facility, a home-health service provider, and others. In some embodiments, a health care organization may include a pharmacy enterprise.

As used herein, the term "customer" indicates someone purchasing a retail product but may additionally be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason or desire to purchase one or more retail products or to perform one or more functions relating to prescription medications, whether the prescriptions are related to a single patient or multiple patients. For example, a customer could be a caregiver responsible for patients with a specific disease that progresses in a known manner. The caregiver customer might greatly benefit from gaining information related to various medications and health products to assist in his or her caregiver responsibilities. In any event, while the term "customer" may be used interchangeably with the term "patient," in this specification the term "patient" is used primarily so as to avoid confusion.

Generally speaking, an automated prescription processing system (also referred to herein as "the system") receives an electronic prescription from a health care organization using electronic medical records (EMRs), electronic health records (EHRs), or standalone e-Prescribing systems. The system automatically converts the information from the electronic prescription into a pharmacy prescription record, which can be filled by a pharmacist at a selected pharmacy location, without requiring a technician to manually enter data from the electronic prescription into the prescription processing system. The automated prescription processing system may convert patient identification information, prescribing physician (also referred to herein as a "prescriber") identification information, medication information, drug quantity, drug days' supply, prescriber instructions and directions for use (Sig) from an electronic prescription format into the pharmacy prescription record. In addition, the automated prescription processing system may determine whether generic substitution of a brand name medication is allowed and substitutes the generic for the brand name medication on the electronic prescription.

Although the automated prescription processing system may receive an electronic prescriptions via a digital network, the format in which the information or data is stored in an electronic prescription may be different from the format in which pharmacy prescription data or records are stored.

Therefore, it may be necessary to convert the data in an electronic prescription into a pharmacy prescription record format.

Turning to FIG. 1, a block diagram of an exemplary computer system architecture for implementing a prescription processing system 100 may include both hardware and software applications, as well as various data communications channels for communicating data between the various hardware and software components. The automated prescription processing system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists, technicians, and other pharmacy personnel, referred to collectively herein simply as "pharmacists" (not shown), use the pharmacy workstations 128 to access customer information, enter new prescriptions, access insurance and payment information and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. The retail network 110 may also include one or more warehouses or central-filling facilities 118. The warehouses or central-filling facilities 118 may distribute medications or retail products to the various retail pharmacies 112 in the retail network 110, or may distribute medications or retail products directly to customers.

Those of ordinary skill in the art will recognize that the front-end components 102 could also comprise a plurality of facility servers 126 disposed at the plurality of pharmacies 112 instead of, or in addition to, a plurality of pharmacy workstations 128. Each of the pharmacies 112 may include one or more facility servers 126 that may facilitate communications between the workstations 128 of the pharmacies 112 via a digital network 130, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126, and vice versa. Moreover, environments other than the pharmacies 112 may employ the workstations 128 and the servers 126. As used herein, the term "pharmacy" refers to any of these environments (e.g., call centers, kiosks, Internet interface terminals, etc.) in addition to the retail pharmacies 112, etc. described above.

The front-end components 102 communicate with the back-end components 104 via the digital network 130. One or more of the front-end components 102 may be excluded from communication with the back-end components 104 by configuration or by limiting access due to security concerns. In some embodiments, the pharmacies 112 may communicate with the back-end components via the digital network 130. In other embodiments, the pharmacies 112 may communicate with the back-end components 104 via the same digital network 130.

Additionally, electronic prescriptions 192 may be transmitted in the form of electronic data files from an EMR data storage entity 190 to the automated prescription processing system 100 via the digital network 130. Alternatively, electronic prescriptions 192 may be transmitted from an EHR data storage entity (not shown) or a standalone e-Prescribing data storage entity (not shown). An electronic prescription 192 corresponding to a particular patient may be an electronic data file and may be used in lieu of or in addition to standard paper prescriptions. Information or data stored in an electronic prescription 192 may include, for example, the patient name, the patient address, the patient birth date, the prescriber name, the prescriber license number, the medication name, the quantity, a days' supply, directions for use, specific instructions from the prescriber, etc. Privacy of patients' EMRs may be privacy protected according to local and/or federal government laws and regulations. The EMR data storage entity 190 may include one or more data storage devices of any known non-transitory, tangible, computer-readable storage media technology (e.g., disks, solid state devices, data banks, servers, cloud storage, etc.). The central processing system 140 or the facility servers 126 may receive the electronic prescriptions 192 via the digital network 130.

The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. The back-end components 104 include the central processing system 140 within a central processing facility, such as, for example, the central processing facility described in U.S. Pat. No. 8,175,891 entitled "DISTRIBUTED PHARMACY PRESCRIPTION PROCESSING SYSTEM" the entire disclosure of which is incorporated by reference herein. Of course, the pharmacies 112 may be communicatively connected to different back-end components 104 having one or more functions or capabilities that are similar to the central processing system 140. The central processing system 140 may include one or more computer processors 162 adapted and configured to execute various software applications and components of the new prescription order system 100, in addition to other software applications.

The central processing system 140 further includes a database 146. The database 146 is adapted to store data related to the operation of the automated prescription processing system 100 (e.g., patient profile data, physician profile data as well as medication data, etc.). In some embodiments, the database 146 may include the pharmacy patient database 200, the pharmacy prescriber database 146 and the pharmacy medication database. The central processing system 140 may access data stored in the database 146 when executing various functions and tasks associated with the operation of the new prescription order system 100. For simplicity, FIG. 1 illustrates the database 146 as only one instance of a database. However, the database 146 according to some implementations includes a group of one or more databases, each storing different information. For example, one database may store patient profile data while another may store physician profile data. For the purposes of this discussion, the term "database" 146 may refer to an individual database or to a group of two or more databases.

Although FIG. 1 depicts the automated prescription processing system 100 as including the central processing system 140 in communication with three pharmacies 112, it should be understood that different numbers of processing systems and pharmacies may be utilized. For example, the digital network 130 (or other digital networks, not shown) may interconnect the central processing system 140 to a plurality of included central processing systems 140 and hundreds of pharmacies 112. According to the disclosed example, this configuration may provide several advantages, such as, for example, enabling near real-time uploads and downloads of information as well as periodic uploads and downloads of information. This provides for a primary backup of all the information generated in the automated pharmacy process. Alternatively, some of the pharmacies 112 may store data locally on the facility server 126 and/or the workstations 128.

FIG. 1 also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner.

The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

The program memory 160 may also contain machine-readable instructions (i.e., software) 171, for execution by the processor 162. The software 171 may perform the various tasks associated with operation of the pharmacy or pharmacies, and may be a single module 171 or a plurality of modules 171A, 171B. While the software 171 is depicted in FIG. 1 as including two modules, 171A and 171B, the software 171 may include any number of modules accomplishing tasks related to pharmacy operation including, for example, receiving prescription orders, managing prescription workflow, etc. In some embodiments, the software 171 may include instructions for implementing the exemplary apparatuses, systems, and methods for reducing return of prescriptions to stock as described herein. The central processing system 140 implements a server application 113 for providing data to a user interface application 111 operating on the workstations 128.

As described above, the database 146, illustrated in FIG. 1, includes various information about the pharmacy's customers, prescribing physicians, and prescription medications. Customer records (e.g., a data structure of FIGS. 4A-4D) are among the exemplary data that the automated prescription processing system 100 may store on the database 146. A customer record contains important information about the customer and the various pharmacy services that have been invoked by, or on behalf of, the customer in a customer profile. The customer profile includes basic biographical information about the customer, such as a customer name, a customer social security number, a customer address, a customer phone number, a customer birth date, customer prescription history, customer allergies, customer insurance information etc. Prescribing physician records may also be stored on the database 146.

Prescribing physician records may include a prescriber name, a practice name, a prescriber DEA number, a prescriber phone number, a prescriber office address, etc. The database 146 may also store a list of predetermined prescriber instruction components. Moreover, prescription medication records may include a medication name, a quantity of the medication, a generic equivalent, whether the medication is a controlled substance, a Dispense as Written (DAW) code, a National Drug Code (NDC), etc.

Figure 2:
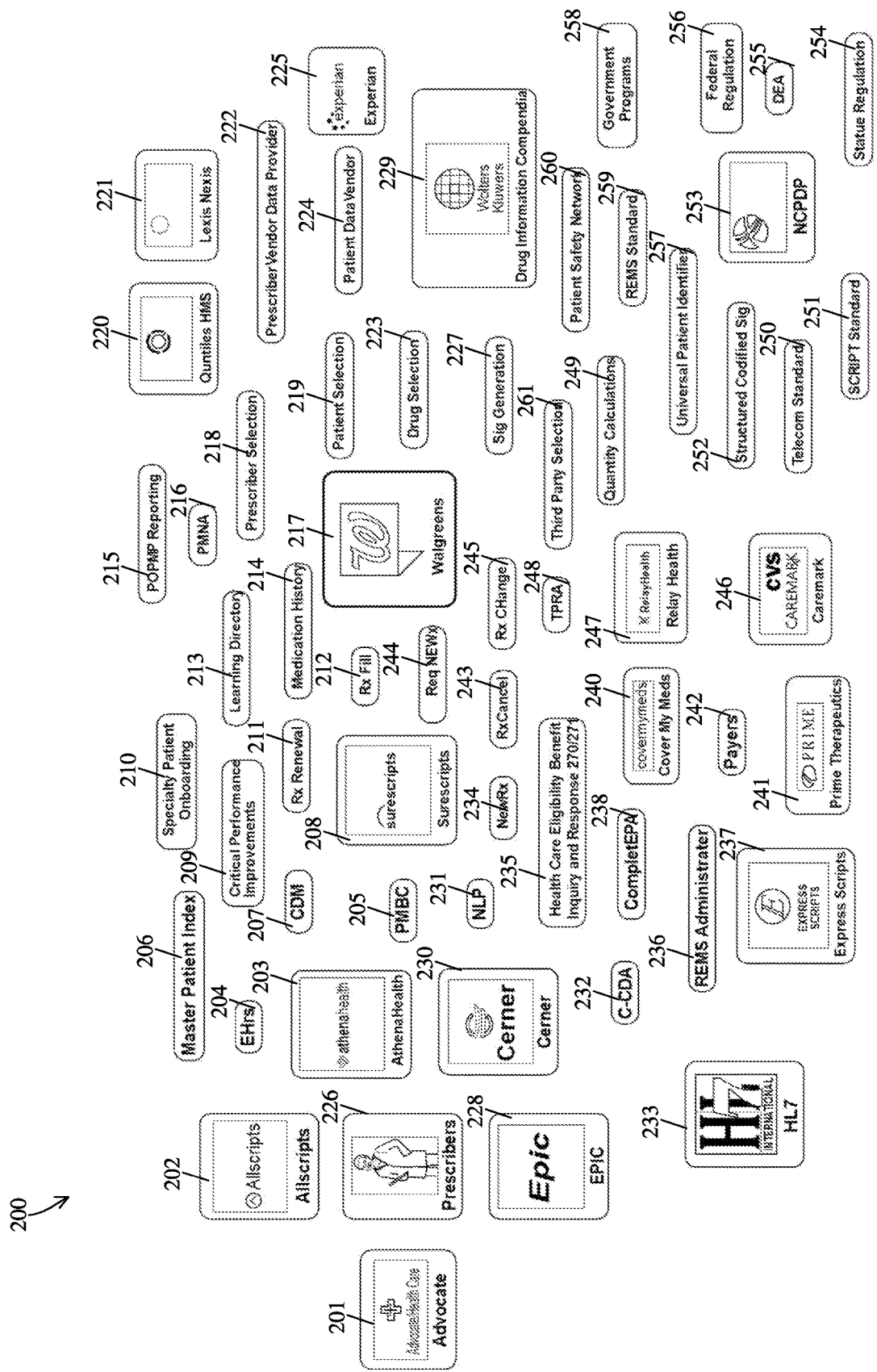
FIG. 2 depicts a high-level block diagram of an example healthcare data source, data transmission, and data reception structure.

With reference to FIG. 2, a high-level block diagram of a healthcare data source, data transmission, and data reception structure 200 may include at least one of: a prescriber (e.g., Advocate) healthcare system 201, an EMR (e.g., Allscripts) data source 202, an EMR (e.g., Athena Health) data source 203, an electronic health records (EHRs) data source 204, a patient medication benefit check (PMBC) data source 205, a master patient index data source 206, a customer data management (CDM) data source 207, a Surescripts data source 208, a critical performance improvements data source 209, a special patient onboarding (SPO) data source 210, a pharmacy dispensing system (Rx renewal) data source 211, a Rx fill method of interchanging electronic information 212, a learning directory data source 213, a medication history data source 214, a prescription drug prescription monitoring program (PDPMP) reporting data source 215, a primary medication non-adherence (PMNA) data source 216, a pharmacy (e.g., Walgreens) data source 217, a prescriber selection data source 218, a patient selection data source 219, a prescriber (e.g., Quintiles IMS (or IQVIA)) data source 220, a prescriber (e.g., Lexis Nexis) data source 221, a prescriber vendor data provider data source 222, a drug selection (e.g., orange book) data source 223, a patient data vendor data source 224, a patient data vendor (e.g., Experian) data source 225, a Prescribers data source 226, a prescriber's instruction (e.g., a Sig) generation data source 227, an EHR (e.g., Epic) data source 228, a drug information compendia (e.g., Wolters Kluwer) data source 229, an EHR (e.g., Cerner) data source 230, a natural language processor (NLP) (e.g., a Stanford University NLP, a Walgreens NLP, etc.) data source 231, a consolidated clinical document architecture (C-CDA) data source 232, a HL7 International data source 233, a NewRx method of exchanging electronic health information 234, a healthcare eligibility benefit inquiry and response 270/271 data source 235, a risk evaluation and mitigation strategy (REMS) data source 236, an Pharmacy Prescription Benefit Manager (PBM) (e.g., Express Scripts, Cigna) data source 237, a patient insurance formulary tool (e.g., CompletEPA) data source 238, a method to electronically obtain prior authorizations (e.g., cover my meds) data source 240, a PBM (e.g., Prime Therapeutics) data source 241, a payers (e.g., a prescription insurance company) data source 242, a Rx Cancel method of electronic health information exchange 243, a request new Rx method of electronic health information exchange 244, a Rx change method of electronic health information exchange 245, a PBM (e.g., CareMark CVS) data source 246, a RelayHealth data source 247, a third party rejection automation (TPRA) data source 248, a quality calculations data source 249, an industry-wide standard for communicating electronic prescription orders (Telecom) data source 250, an industry-wide standard for communicating electronic prescription (SCRIPT) data source 251, a structure codified Sig (e.g., a Walgreens) data source 252, a national council for prescription drug programs (NCPDP) source of pharmacy industry technology standards 253, a state regulation data source 254, a drug enforcement agency (e.g., DEA) data source 255, a federal regulation data source 256, a universal patient identifier data source 257, a government programs (e.g., Medicare, Medicaid, WIC, etc.) data source 258, a REMS standard data source 259, a patient safety network data source 260, a third party selection data source 261, any sub-combination thereof, or a combination thereof. The healthcare data source, data transmission, and data reception structure 200 may also include a prescription drug monitoring program (PDMP) data source, a clinical document architecture (CDA) data source, a fast healthcare interoperability resources (FHIR) data source, a national record locator service (e.g., NRLS) data source, a specialty patient onboarding (SPO) data source, and/or a healthcare accounts receivable (HAR) data source. Any of the data sources 201-261 of FIG. 2 may be, for example, stored in a databased (e.g., database 146 of a central processing system 140 of FIG. 1).

A "special patient" may be determined based on, for example, a prescribed medication. For example, with respect to Bupropion (Zyban), special patient groups may include: children and adolescents, elderly individuals, hepatically impaired individuals, renally impaired individuals, psychiatric individuals, pregnant or lactating women, individuals that are predisposed towards seizure, and individuals with eating disorders. Drug utilization rules for Bupropion (Zyban) may include: children and adolescents, not recommended in patients under 18 yrs of age; elderly, use with caution, increased sensitivity may be an issue (more likely to have decreased renal function), 150 mg once daily is recommended; hepatically impaired individuals, contraindicated in patients with severe hepatic cirrhosis (reduced clearance leading to high plasma levels), use with caution in mild-to-moderate hepatic impairment, which may lead to higher levels, 150 mg daily is recommended, monitor closely for possible undesirable effects (e.g., insomnia, dry mouth, seizures) indicating high drug metabolite levels; renally impaired individuals, use with caution, 150 mg once daily recommended, monitor closely for possible undesirable effects (e.g., insomnia, dry mouth, seizures) indicating high drug metabolite levels; psychiatric individuals, contraindicated in patients with a history of bipolar disorder, may precipitate psychotic episodes in susceptible patients, use with caution; pregnant or lactating women, Zyban must not be used in pregnancy/lactation, if pharmacotherapy is required consider NRT, which is also contraindicated in some products, but safer than smoking in pregnancy; individuals that are predisposed towards seizure, contraindicated in patients with current or previous seizure disorder, use with extreme caution in patients with certain conditions including: a history of brain trauma, brain injury, concomitant administration of medicines known to lower the seizure threshold (e.g., antipsychotics, antidepressants such as SSRIs, theophylline, systemic steroids, etc.), also use with caution in circumstances of: alcohol abuse, abrupt withdrawal from alcohol/benzodiazepines, diabetes treated with hypoglycemics/insulin (reduce dose to 150 mg per day), use of stimulants/anorectic products; and individuals with eating disorders, contraindicated in patients with current or previous diagnosis of bulimia or anorexia nervosa. Sensitivity may require the medication to be contraindicated in patients with current hypersensitivity to Zyban or excipients in the tablets (excipients do not include lactose). Discontinue if patient experiences hypersensitivity or anaphylactic reactions (e.g., rash, pruritis, urticaria, chest pain, oedema or dyspnea).

Turning to FIG. 3, an exemplary electronic prescription (eRx) 300 for a particular patient 102 is illustrated on a display of a user device 301. This is merely an example and electronic prescriptions may be formatted in any suitable number of ways. Electronic prescribing (e-prescribing or eRx) may be a computer-based electronic generation, transmission, and filling of a medical prescription, taking the place of paper, verbal and faxed prescriptions. E-prescribing allows a physician, nurse practitioner, or physician assistant (prescribers) to use digital prescription software to electronically transmit a new prescription or renewal authorization to a community or mail-order pharmacy. It outlines the ability to send error-free, accurate, and understandable prescriptions electronically from the healthcare provider to the pharmacy. E-prescribing is meant to reduce the risks associated with traditional prescription script writing. It is also one of the major reasons for the push for electronic medical records. By sharing medical prescription information, e-prescribing seeks to connect the patient's team of healthcare providers to facilitate knowledgeable decision making. According to NCPDP Electronic Prescribing Standards, a "qualified" e-prescribing system must be capable of performing all of the following functions: patient identification; generating a complete active medication list, possibly incorporating electronic data received from an insurance provider; access to patient historical data; prescribe or add new medication and select the pharmacy where the prescription will be filled; work with an existing medication within the practice, this can involve viewing details of a medication, remove a medication from the active medication list, change dose, etc., for a medication or renew one or more medications; printing prescriptions; electronically transmitting prescriptions to a transaction hub; conducting all safety checks using an integrated decision support system (often known as a Drug Utilization Review); safety checks (i.e., automated prompts that offer information on the drug being prescribed, potential inappropriate dose or route of administration, drug-drug interactions, allergy concerns, or warnings of caution, etc.); flagging availability of lower cost, therapeutically appropriate alternatives (if any); providing information on formulary or tiered formulary medications, patient eligibility, and authorization requirements received electronically from the patient's insurance provider; system integration capabilities (e.g., connection with various databases, connection with pharmacy and pharmacy benefit manager systems); and educational capabilities (e.g., patient education, provider feedback).

Although the automated prescription processing system 100 may receive electronic prescriptions via a digital network, the format in which the information or data is stored in an electronic prescription is often different from the format in which pharmacy prescription data or records are stored. Therefore, it may be necessary to convert the data in an electronic prescription into a pharmacy prescription record format. In the example of FIG. 3, the electronic prescription 100 includes several data fields which may be grouped into multiple prescription components for the automated prescription processing system. The prescription components include patient information, prescriber information, medication name information, quantity and days' supply and prescriber instructions.

For example, a patient name field 302, a patient age field 304, and a patient address field 308 may fit within the patient information component. On the other hand, a prescriber name field 316, a DEA registration field 318, a prescriber license number field 320, a prescriber phone number field 322, and a prescriber facility field 324 may fit within the prescriber information component. Electronic prescription data which may fit within the medication name information component includes a medication name 310, a medication quantity 330 and a dispense as written (DAW) field 326 which is used to determine whether a generic substitute is permitted. The DAW field 326 may also include a notification (e.g., a text message, a tweet, a Facebook post, an email, a telephone call, etc.) to a patient that a prescription for the patient has been received at a pharmacy along with a request from the pharmacy for the patient to acknowledge whether the patient will actually purchase the prescription. The patient may, for example, use the write, print, renew, transmit selection icons to input and transmit a response to the pharmacy. Additionally, a number of days field 328 and a dispense (DISP) field 314 may fit within the days' supply and quantity components, respectively, while a prescriber directions (Sig) field 312 may fit within the prescriber instructions component. The electronic prescription 300 may also include an indication of a pharmacy location for the patient to pick up the prescription. Alternatively, the pharmacy location may default to the closest location to the patient address 308.

An automated prescription processing system 100 may detect data by parsing the electronic prescription 300 to find field identifiers and XML tags corresponding to data fields. For example, the electronic prescription 300 may follow the SCRIPT 251 standard defined and maintained by the National Council for Prescription Drug Programs (NCPDP) 253, which defines field identifiers and XML tags for each data field. For example, the system may parse the electronic prescription 300 for an XML tag or field identifier indicating a DEA 255 registration field. However, this is merely one example of how data within an electronic prescription may be detected and categorized by the automated prescription processing system. Alternatively, data may be detected and categorized in any suitable number of ways and in some implementations data from the electronic prescription may not be categorized. For case of illustration only, this application will continue to describe detecting data from an electronic prescription in the manner described above.

Turning to FIGS. 4A-4D, a data structure 400*a-d* may include a plurality of data attributes 405*a-d*. At least some of the data attributes 405*a-d* may include a respective data attribute business description 410*a-d* and/or respective comments and follow-ups 415*a-d*. The individual data attributes 405*a-d* may, for example, include whether the prescription is accepted by an insurance of a patient (ACCEPT), whether the prescription has been previously automatically refilled (AUTO_PRE_IND), an average prescription count for a pharmacy (AVG_RX_CNT_CY), an average number of days between when a prescription was entered into a pharmacy system and when the prescription was sold within the past twelve months (AVG_SOLDGAP_PRE), whether the prescription is associated with a brand medication (BRAND_MED), whether a patient will pay cash for a prescription (CASH), whether a prescription was review by a central processing center (CENTRAL CONTROL), whether an associated pharmacy is a large volume store (COMMERCIAL), whether it is predictable that a prescription will be deleted, returned to stock-dependent variable (DELETE), whether demographic information for a patient is missing (DEMO_MISS_IND), whether the prescription is for a dental patient (DENTAL), whether the prescription is for a for a dermatologist patient (DERMATOLOGIST), whether a drug indication is missing from a prescription (DRUG_MISS_IND), whether a prescription includes a dispense/fill indication (DSPN_FILL_NBR), whether an email address for a patient is available (EMAIL_IND), whether the prescription is associated with an emergency room patient (ER), whether the prescription is an emergency prescription (ESCRIPT_IND), whether the prescription is related to an eye or nose of a patient (EYE_NOSE), whether a patient is female (FEMALE), how may days is the prescription for (FILL_DAYS_SUPPLY), whether a prescription fill date is entered (FILL_ENTER_DT), a prescription out-of-pocket cost to patient (FILL_LABEL_PRICE_DLRS), whether the prescription is for tetracyclines (GPI04), whether the prescription is for fluoroquinolones (GPI05), whether the prescription is for penicillins (GPI10), whether the prescription is for antifungals (GPI11), whether the prescription is for antivirals (GPI12), whether the prescription is for anti-infective agents-miscellaneous (GPI16), whether the prescription is for vaccines (GPI17), whether the prescription is for cephalosporins (GPI20), whether the prescription is for corticosteroids (GPI22), whether the prescription is for contraceptives (GPI25), whether the prescription is for antidiabetics (GPI27), whether the prescription is for macrolides (GPI30), whether the prescription is for beta blockers (GPI33), whether the prescription is for calcium channel blockers (GPI34), whether the prescription is for antihypertensives (GPI36), whether the prescription is for diuretics (GPI37), whether the prescription is for antihyperlipidemics (GPI39), whether the prescription is for antihistamines (GPI41), whether the prescription is for nasal agents-systemic and topical (GPI42), whether the prescription is for cough/cold/allergy (GPI43), whether the prescription is for antiasthmatic and bronchodilator agents (GPI44), whether the prescription is for laxatives (GPI46), whether the prescription is for ulcer drugs (GPI49), whether the prescription is for antiemetics (GPI50), whether the prescription is for urinary anti-infectives (GPI53), whether the prescription is for genitourinary agents-miscellaneous (GPI56), whether the prescription is for antianxiety agents (GPI57), whether the prescription is for antidepressants (GPI58), whether the prescription is for ADHD/anti-narcolepsy/anti-obesity/anorexiants (GPI61), whether the prescription is for analgesics-opioid (GPI65), whether the prescription is for analgesics-anti-inflammatory (GPI66), whether the prescription is for anticonvulsants (GPI72), whether the prescription is for musculoskeletal therapy agents (GPI75), whether the prescription is for ophthalmic agents (GPI86), whether the prescription is for mouth/throat/dental agents (GPI88), whether the prescription is for dermatologicals (GPI90), whether the prescription is for medical devices and supplies (GPI97), whether the prescription is for internal medication (INTERNAL), whether a patient is from a rural/urban, or suburban area (LOC_AREA_TYPE), whether the prescription is for a maintenance medication (MAINT_MED), a median income of a patient (MEDIAN_H_INCOME), whether patient is covered by Medicaid (MEDICAID), a total prescription filled for a patient in past twelve months (N_EPISODE_PRE), a total prescription return/delete for patient in past twelve months (N_RTS_PRE), a total prescription sold count in past twelve months (N_SOLD_PRE), is prescription to be administered by a nurse (NURSE), is prescription associated with an ObGyn physician (OBGYN), whether pharmacy associated with prescription is open twenty-four hours/day (OPEN_24), whether patient is covered by Medicare part D (PARTD), a patient age (PAT_AGE), a patient identification (PAT_ID), a patient band range age (PBR_AGE), a patient band range class (PBR_CLASS), a patient band range sex (PBR_FEMALE), whether prescription is associated with a pedestrian (PE- DIATRIAN), whether a patient phone number is identified (PHONE_IND), a number of days between most recent sold date and an index date-indexed date that triggered to the system same as entered date (RECENCY), a total prescription count of a day-counts of all medication received both filled and new (RX_CNT), date a prescription was created (RX_CREATE_DT), a prescription DAW indication (RX_DAW_IND), a patient NBR fill (RX_FILL_NBR), whether a prescription indication is missing IND (RX_MISS_IND), a prescription NBR (RX_NBR), whether there is an over the counter alternative for the prescription (RX_OTC_ALT), whether the prescription is for a specialty drug (SPCLTY_DRUG_IND), whether the prescription is for a STAR drug (STAR), a patient NBR (STR_NBR), whether a prescription is associated with a surgeon (SURGON), whether a text message number is available for a patient (TXT_MSG_IND), whether a patient is a waiter (WAITER), a patient week (WEEK), whether the prescription is associated with a weekend (WEEKEND_IND), any sub-combination thereof, or a combination thereof.

Figure 5A:
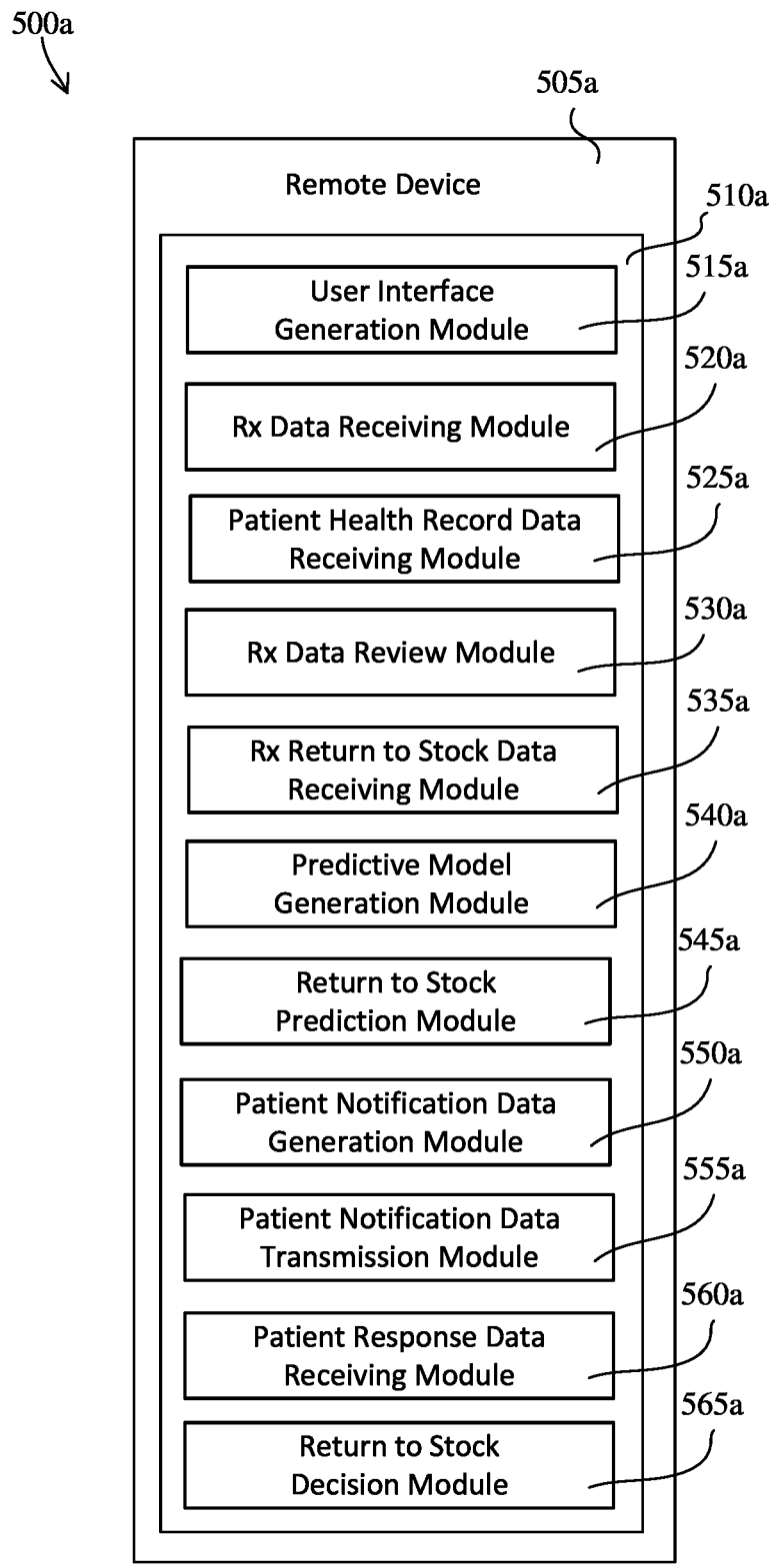
FIG. 5A depicts a block diagram for an example remote computing device for use in generating a predictive model for reducing return of prescriptions to stock.

With reference to FIG. 5A, a computer system for implementing an automated prescription processing system 500a may include a remote device 505a. The remote device 505a may be similar to, for example, any one of a controller (e.g., controller 155 of FIG. 1), a workstation (e.g., workstation 128 of FIG. 1), a cellular telephone, a personal electronic device, or a combination thereof. In any event, the remote device 505a may include a user interface generation module 515a, a prescription (e.g., cRx) data receiving module 520a, a patient health record data receiving module 525a, a prescription review module 530a, a prescription return to stock data receiving module 535a, a predictive model generation module 540a, a return to stock prediction module 545a, a patient notification data generation module 550a, a patient notification data transmission module 555a, a patient response data receiving module 560a, and a return to stock decision module 565a, for example, stored on a memory 510a as a set of computer-readable instructions. The memory 510a may be similar to, for example, the memory 160 or 171 of FIG. 1. Alternatively, any one of the modules 515a-565a may be configured as a dedicated hardware device (e.g., an application specific integrated circuit (ASIC), a logic circuit, an electrical circuit made up of discrete components, a field programmable gate array (FPGA), a hardware module, a sub-combination thereof, or a combination thereof, etc.).

Figure 5B:
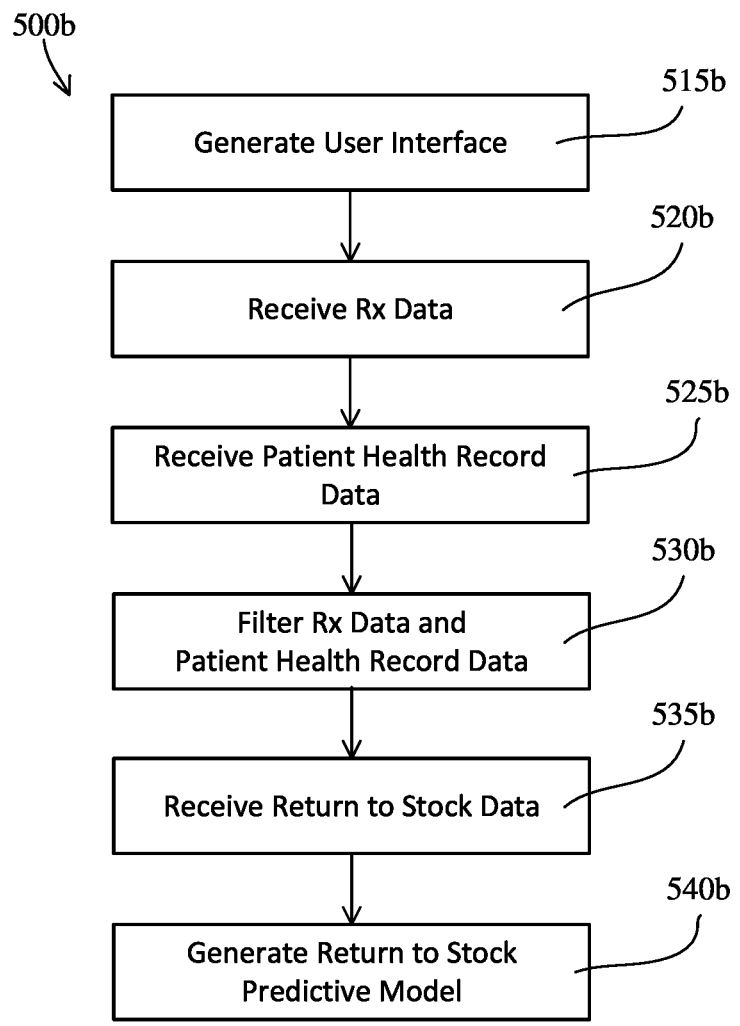
FIG. 5B depicts an example method for generating a predictive model for reducing return of prescriptions to stock.

Turning to FIG. 5B, a computer implemented method for generating a prescription return to stock predictive model 500b may be implemented by, for example, the remote device 505a. In particular, a processor (e.g., processor 162 of FIG. 1) may execute the user interface generation module 515a to, for example, cause the processor 162 to generate a predictive model display generation user interface (block 515b). For example, a predictive model generation user interface may include, for example, display of a user selectable icon, on a touch screen display device, that enables a user to launch a predictive model generation application.

The processor 162 may execute the prescription data receiving module 520a to, for example, cause the processor 162 to receive prescription data (block 520b). For example, the processor 162 may receive prescription data from a pharmacy database and/or a third party database (e.g., any of the data sources of FIG. 2). The prescription data may be representative of a plurality of previously processed prescriptions for a cohort of patients. The processor 162 may execute the prescription data receiving module 520a in response to, for example, a user activating a predictive model generation application (block 520b). The prescription data may be, for example, representative of: whether a prescription is a eRx or written Rx; whether a prescription is refill by autofill, IVR, or internet; whether a prescription is associated with cash payment; whether a prescription is associated with insurance (reject or accept); what payment type a prescription is associated with (e.g., commercial or government); what medication type a prescription is associated with; whether a prescription is associated with a copay; number of days' supply associated with a prescription; whether a prescription is associated with acute or chronic; whether a prescription is associated with brand or generic; what drug manufacturer a prescription is associated with; whether a prescription is associated with a unique Rx count/day; whether a prescription is associated with a week day or weekend impact; a sub-combination thereof, or a combination thereof.

The processor 162 may execute the patient health record data receiving module 525a to, for example, cause the processor 162 to receive patient health record data (block 525b). For example, the processor 162 may receive patient health record data from a pharmacy database and/or a third party database (e.g., any of the data sources of FIG. 2). The patient health record data may be representative of a plurality of patient health records associated with previously processed prescriptions for a cohort of patients. The processor 162 may execute the patient health record data receiving module 525a in response to, for example, a user activating a predictive model generation application (block 525b). The patient health record data may be representative of a patient medication history (e.g., a most recent prescription fill date, a total prescription sold fill counts in the previous year, etc.). Alternatively, or additionally, the patient health record data may be representative of patient demographics (e.g., patient age, patient gender, patient median household income, etc.). Alternatively, or additionally, the patient health record data may be representative of provider demographics (e.g., provider age, provider gender, a prescription dispense as written (DAW) indication, a provider's specialty, etc.). Alternatively, or additionally, the patient health record data may be representative of missing prescription value indicators.

The processor 162 may execute the prescription data review module 530a to, for example, cause the processor 162 to filter the prescription data and/or the patient health record data (block 530b). For example, the processor 162 may receive a plurality of the data attributes 405a-d and may filter a number of variables actually used to generate an associated predictive model. The processor 162 may execute the prescription return to stock data receiving module 535a to, for example, cause the processor 162 to receive return to stock data (block 535b). The return to stock data may be, for example, representative of whether any given prescription, that is included within the prescription data, was returned to stock.

The processor 162 may execute the predictive model generation module 540a to, for example, cause the processor 162 to generate a predictive model (block 540b). The predictive model may be based on the prescription data, the patient health record data, the filtered prescription data, the filter patient health record data, the return to stock data, a sub-combination thereof, or a combination thereof. The predictive model may be, for example, an extreme gradient boosting model, a neural network model, a decision tree model, a regression model, a stepwise regression model, a probability function, a sub-combination thereof, or a combination thereof.

As another particular example, the predictive model may be based on, for example, sixty-six total variables filtered to fifty-two variables. The top twenty risk factors for indicating whether an associated prescription may be returned to stock may, for example, include: whether a prescription was subject to insurance reject, whether patient not insured (Cash Pay), whether a prescription is for MYLAN (Manufacturer), whether a prescription is to AutoFill (Refill channel), whether a prescription is being refilled too soon (Refill channel), whether a prescription requires a copay (log transformation), whether a prescription is for NASAL AGENTS-SYSTEMIC AND TOPICAL, whether a prescription is for ANTIVIRALS, whether a prescription is for ANTIHYPER-LIPIDEMICS, whether a prescription is for ANALGESICS—ANTI-INFLAMMATORY, whether a prescription is for OPHTHALMIC AGENTS, whether a prescription is for DIURETICS, whether a prescription is for MUSCULO-SKELETAL THERAPY AGENTS, whether a prescription is for DERMATOLOGICALS, whether a prescription is for ANTICONVULSANTS, whether a prescription is for VALAENT (Manufacturer), whether a prescription is for ANTIPSYCHOTICS/ANTIMANIC AGENTS, what is a Median Household Income for an associated patient is <30K (GIS proxy), whether a prescription is for Brand Medication, and whether a prescription is for ANTIASTHMATIC AND BRONCHODILATOR AGENTS.

As another example, a predictive model may be based on, for example, sixty-three total variables filtered to thirty-nine variables. The top ten risk factors for indicating whether an associated prescription may be returned to stock may include: whether an associated prescription is subject to an insurance reject, whether patient not insured (Cash Pay), whether a prescription requires a copay (log transformation), what is a Median Household Income for an associated patient is <30K (GIS proxy), whether a prescription is for Brand Medication, whether a prescription is for MYLAN (Manufacturer), whether a prescription is for VALAENT (Manufacturer), whether a prescription is received via eRx, whether a prescription is for LAXATIVES, and whether a prescriber associated with a prescription is an ER doctor.

As a further example, a predictive model may be based on, for example, fifty-three total variables filtered to thirty-four variables. The top fifteen risk factors for indicating whether an associated prescription may be returned to stock may include: whether an associated prescription is subject to an insurance reject, whether patient not insured (Cash Pay), whether a prescription requires a copay (log transformation), whether a prescription fill channel is missing, what is a Median Household Income for an associated patient is <30K (GIS proxy), whether a prescription is received via eRx, whether a prescription is for ANTIDIABETICS, whether a prescription is for Brand Medication, whether a prescription is for ANALGESICS-ANTI-INFLAMMATORY, whether a prescriber associated with a prescription is an ENT/Eye doctor, whether a prescriber associated with a prescription is a pediatrician, whether a prescription is for ANTIHYPER-LIPIDEMICS, whether a prescription is for DERMATO-LOGICALS, whether a prescriber associated with a prescription is an internal doctor, and what is a prescriptions count filled on the same index day.

Cash payer, higher copay, lower income area where patients live, brand medication may be common risk factors associated with higher delete rates (e.g., prescription return to stock) for new to WAG patients, new to GPI6 patients, and/or refill patients. An eRx may be associated with higher delete risk for new to WAG and new to GPI6 patients. Autofill and certain manufacturers such as Mylan and Valeant, may be correlated with higher delete rates (e.g., prescription return to stock) for refill patients. Prescriptions that were rejected by an insurance company may be a highest indicator for deletes (e.g., prescription return to stock) among all three groups.

Figure 5C:
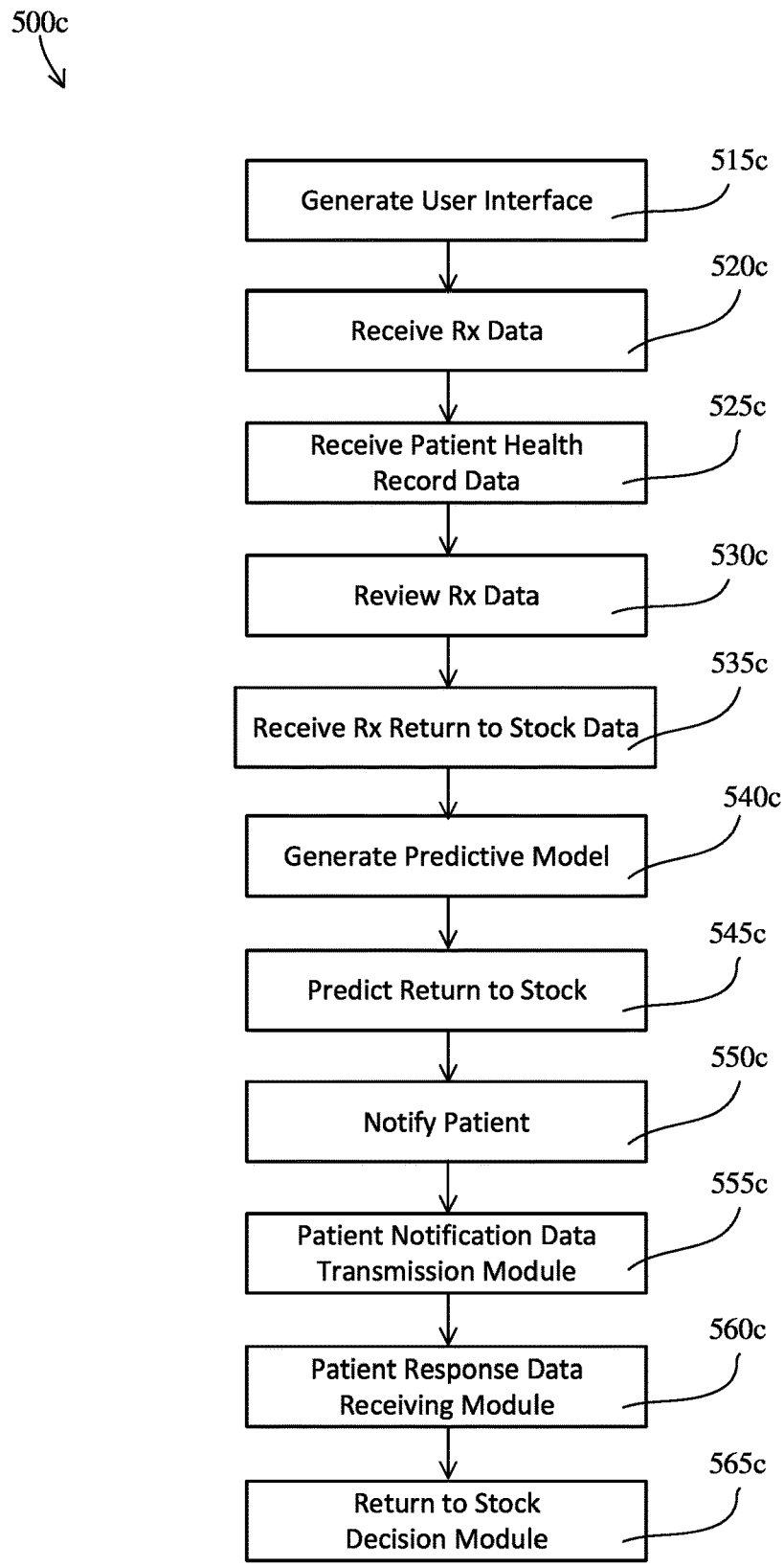
FIG. 5C depicts an example method for processing a prescription.

With reference to FIG. 5C, a computer implemented method for processing a prescription 500c may be implemented by, for example, the remote device 505a. In particular, a processor (e.g., processor 162 of FIG. 1) may execute the user interface generation module 515a to, for example, cause the processor 162 to generate a predictive model display generation user interface (block 515c). For example, a predictive model generation user interface may include, for example, display of a user selectable icon, on a touch screen display device, that enables a user to launch a predictive model generation application.

The processor 162 may execute the prescription data receiving module 520a to, for example, cause the processor 162 to receive prescription data (block 520c). For example, the processor 162 may receive prescription data from a pharmacy database and/or a third party database (e.g., any of the data sources of FIG. 2). The prescription data may be representative of a current prescription and a plurality of previously processed prescriptions for a cohort of patients. The processor 162 may execute the prescription data receiving module 520a in response to, for example, a user activating a predictive model generation application (block 520c). The prescription data may be, for example, representative of: whether a prescription is a cRx or written Rx; whether a prescription is refill by autofill, IVR, or internet; whether a prescription is associated with cash payment; whether a prescription is associated with insurance (reject or accept); what payment type a prescription is associated with (e.g., commercial or government); what medication type a prescription is associated with; whether a prescription is associated with a copay; number of days' supply associated with a prescription; whether a prescription is associated with acute or chronic; whether a prescription is associated with brand or generic; what drug manufacturer a prescription is associated with; whether a prescription is associated with a unique Rx count/day; whether a prescription is associated with a week day or weekend impact; a sub-combination thereof, or a combination thereof.

The processor 162 may execute the patient health record data receiving module 525a to, for example, cause the processor 162 to receive patient health record data (block 525c). For example, the processor 162 may receive patient health record data from a pharmacy database and/or a third-party database (e.g., any of the data sources of FIG. 2). The patient health record data may be representative of health records associated with a current patient/prescription and a plurality of patient health records associated with previously processed prescriptions for a cohort of patients. The processor 162 may execute the patient health record data receiving module 525a in response to, for example, a user activating a predictive model generation application (block 525c). The patient health record data may be representative of a patient medication history (e.g., a most recent prescription fill date, a total prescription sold fill counts in the previous year, etc.). Alternatively, or additionally, the patient health record data may be representative of patient demographics (e.g., patient age, patient gender, patient median household income, etc.). Alternatively, or additionally, the patient health record data may be representative of provider demographics (e.g., provider age, provider gender, a prescription dispense as written (DAW) indication, a provider's specialty, etc.). Alternatively, or additionally, the patient health record data may be representative of missing prescription value indicators.

The processor 162 may execute the prescription data review module 530*a* to, for example, cause the processor 162 to filter the prescription data and/or the patient health record data (block 530*c*). For example, the processor 162 may receive a plurality of the data attributes 405*a-d* and may filter a number of variables actually used to generate an associated predictive model. The processor 162 may execute the prescription return to stock data receiving module 535*a* to, for example, cause the processor 162 to receive return to stock data (block 535*c*). The return to stock data may be, for example, representative of whether any given prescription, that is included within the prescription data, was returned to stock.

The processor 162 may execute the predictive model generation module 540*a* to, for example, cause the processor 162 to generate a predictive model (block 540*c*). The predictive model may be based on the prescription data, the patient health record data, the filtered prescription data, the filter patient health record data, the return to stock data, a sub-combination thereof, or a combination thereof. The predictive model may be, for example, an extreme gradient boosting model, a neural network model, a decision tree model, a regression model, a stepwise regression model, a probability function, a sub-combination thereof, or a combination thereof.

An extreme, or lite, gradient boosting may be, for example, a machine learning technique for regression and classification problems (e.g., predicting whether a prescription will be returned to stock), which produces a prediction model in the form of an ensemble of weak prediction models, typically decision trees. Extreme, or lite, gradient boosting may build a model in a stage-wise fashion like other boosting methods do, and may generalize the models by allowing optimization of an arbitrary differentiable loss function.

A neural network model may be, for example, a network or circuit of neurons, or in a modern sense, an artificial neural network, composed of artificial neurons or nodes. Thus a neural network may be an artificial neural network, for solving artificial intelligence (AI) problems (e.g., predicting whether a prescription will be returned to stock). The connections of the biological neuron are modeled as weights. A positive weight reflects an excitatory connection, while negative values mean inhibitory connections. All inputs are modified by a weight and summed. This activity is referred as a linear combination. Finally, an activation function controls the amplitude of the output. For example, an acceptable range of output is usually between 0 and 1, or it could be −1 and 1.

A decision tree model may be, for example, a decision support tool that uses a tree-like model of decisions and their possible consequences, including chance event outcomes (e.g., predicting whether a prescription will be returned to stock), resource costs, and utility. It is one way to display an algorithm that may contain only conditional control statements.

A regression model may be, for example, a set of statistical processes for estimating the relationships between a dependent variable (often called the 'outcome variable') (e.g., predicting whether a prescription will be returned to stock) and one or more independent variables (often called 'predictors', 'covariates', or 'features') (e.g., variables of FIGS. 4A-D). The most common form of regression analysis is linear regression, in which a researcher finds the line (or a more complex linear function) that most closely fits the data according to a specific mathematical criterion. For example, the method of ordinary least squares computes the unique line (or hyperplane) that minimizes the sum of squared distances between the true data and that line (or hyperplane). For specific mathematical reasons (see linear regression), this allows the researcher to estimate the conditional expectation (or population average value) of the dependent variable when the independent variables take on a given set of values. Less common forms of regression use slightly different procedures to estimate alternative location parameters (e.g., quantile regression or Necessary Condition Analysis) or estimate the conditional expectation across a broader collection of non-linear models (e.g., nonparametric regression). Regression analysis is primarily used for two conceptually distinct purposes. First, regression analysis is widely used for prediction and forecasting, where its use has substantial overlap with the field of machine learning. Second, in some situations regression analysis can be used to infer causal relationships between the independent and dependent variables. Importantly, regressions by themselves only reveal relationships between a dependent variable and a collection of independent variables in a fixed dataset. To use regressions for prediction or to infer causal relationships, respectively, a researcher must carefully justify why existing relationships have predictive power for a new context or why a relationship between two variables has a causal interpretation. The latter is especially important when a researcher hopes to estimate causal relationships using observational data.

Model building techniques may include, for example, fitting regression models in which the choice of predictive variables is carried out by an automatic procedure. In each step, a variable (e.g., a variable of FIGS. 4A-D) may be considered for addition to or subtraction from the set of explanatory variables based on some pre-specified criterion. This may, for example, take the form of a sequence of F-tests or t-tests, but other techniques are possible, such as adjusted R2, Akaike information criterion, Bayesian information criterion, Mallows's Cp, PRESS, or false discovery rate.

A probability function model may be, for example, a mathematical function that provides probabilities of occurrence of different possible outcomes in an experiment (e.g., predicting whether a prescription will be returned to stock). A probability distribution may be a description of a random phenomenon in terms of the probabilities of events. For instance, if the random variable X is used to denote the outcome of a coin toss ("the experiment"), then the probability distribution of X would take the value 0.5 for X=heads, and 0.5 for X=tails (assuming the coin is fair). Examples of random phenomena can include the results of an experiment or survey.

The processor 162 may execute the predict return to stock module 545*a* to, for example, cause the processor 162 to predict whether a prescription will be returned to stock (block 545*c*). For example, the processor 162 may receive prescription data (block 520*c*) and/or patient health record data (block 525*c*), that is representative of a current prescription/patient, and may implement an associated predictive model based on the current prescription data and/or patient health record data to determine whether or not the patient will actually pick-up a medication and/or medical device associated with the prescription.

Alternatively, or additionally, the processor 162 may receive prescription data (block 520*c*) and/or patient health record data (block 525*c*), that is representative of a current prescription/patient, and may implement an associated predictive model based on the current prescription data and/or patient health record data to determine a probability as to whether or not the patient will actually pick-up a medication and/or medical device associated with the prescription. The processor 162 may implement a plurality of predictive models (e.g., an extreme gradient boosting model, a neural network model, a decision tree model, a regression model, a stepwise regression model, a probability function model, etc.) and may base a final determination as to whether or not the patient will actually pick-up the medication and/or medical device based on outputs of a plurality of the predictive models (e.g., an average of the outputs, a weighted average of the outputs, a majority voting of the outputs, etc.).

The processor 162 may execute the patient notification data generation module 550a to, for example, cause the processor 162 to generate patient notification data (block 550c). For example, the processor 162 may generate patient notification data (block 550c) based on a patient preference for receiving a notification via a text message, an email message, a tweet, a Facebook message, etc. The patient notification data may be representative of a notification to the patient that a prescription for the patient has been received by a pharmacy. The processor 162 may execute the patient notification data transmission module 555a to, for example, cause the processor 162 to transmit the patient notification data to a user device (block 555c).

The processor 162 may execute the patient response data receiving module 560a to, for example, cause the processor 162 to receive patient response data (block 560c). The patient response data may, for example, be generated/transmitted by a user device (e.g., user device 605a of FIG. 6A) as discussed with reference to FIGS. 6A and 6B. In any event, the patient response data may be indicative of the patient's intention to actually pick-up a medication and/or medical device associated with a prescription. The processor 162 may execute the return to stock decision module 565a to, for example, cause the processor 162 to determine whether or not a prescription should actually be filled (block 565c). For example, the processor 162 may determine whether or not a prescription should actually be filled based on the predict return to stock and/or the patient response data (block 565c).

Figure 5D:
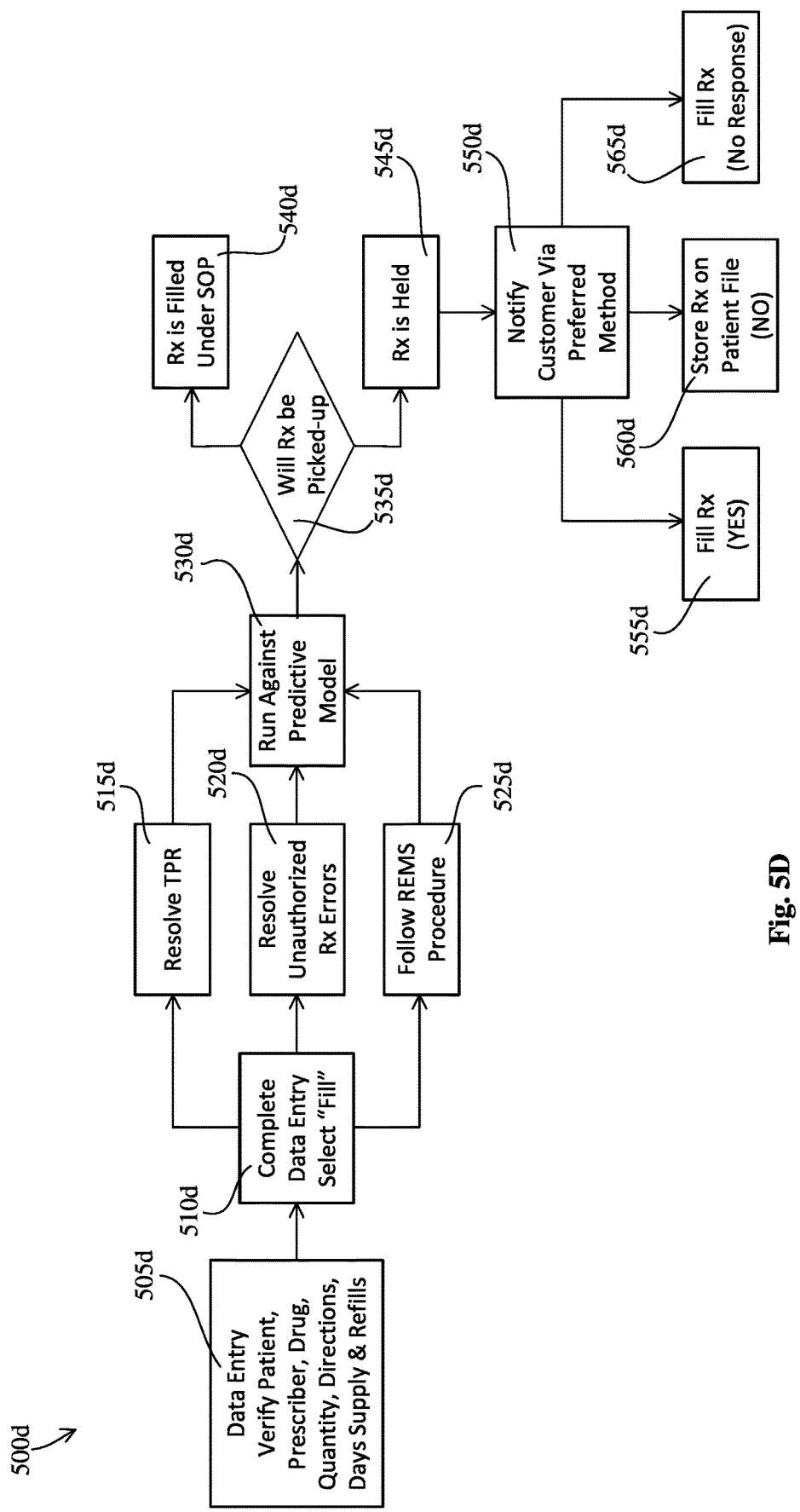
FIG. 5D depicts another example method for processing a prescription.

Turning to FIG. 5D, a computer implemented method for processing a prescription 500d may be implemented by, for example, the remote device 505a. In particular, a processor (e.g., processor 162 of FIG. 1) may execute the prescription data receiving module 520a to, for example, cause the processor 162 to receive prescription data (block 505d). For example, the processor 162 may receive prescription data from a pharmacy database and/or a third party database (e.g., any of the data sources of FIG. 2). The prescription data may be representative of a current prescription for a patient. The processor 162 may execute the prescription data receiving module 520a in response to, for example, a user activating a predictive model generation application. The prescription data may be, for example, representative of: whether a prescription is a eRx or written Rx; whether a prescription is refill by autofill, IVR, or internet; whether a prescription is associated with cash payment; whether a prescription is associated with insurance (reject or accept); what payment type a prescription is associated with (e.g., commercial or government); what medication type a prescription is associated with; whether a prescription is associated with a copay; number of days' supply associated with a prescription; whether a prescription is associated with acute or chronic; whether a prescription is associated with brand or generic; what drug manufacturer a prescription is associated with; whether a prescription is associated with a unique Rx count/day; whether a prescription is associated with a week day or weekend impact; a sub-combination thereof, or a combination thereof.

The processor 162 may execute the patient health record data receiving module 525a to, for example, cause the processor 162 to receive patient health record data (block 510d). For example, the processor 162 may receive patient health record data from a pharmacy database and/or a third party database (e.g., any of the data sources of FIG. 2). The patient health record data may be representative of a health records for a current patient and associated with a current prescription for the patient. The processor 162 may execute the patient health record data receiving module 525a in response to, for example, a user activating a prescription processing application (block 510d). The patient health record data may be representative of a patient medication history (e.g., a most recent prescription fill date, a total prescription sold fill counts in the previous year, etc.). Alternatively, or additionally, the patient health record data may be representative of patient demographics (e.g., patient age, patient gender, patient median household income, etc.). Alternatively, or additionally, the patient health record data may be representative of provider demographics (e.g., provider age, provider gender, a prescription dispense as written (DAW) indication, a provider's specialty, etc.). Alternatively, or additionally, the patient health record data may be representative of missing prescription value indicators.

The processor 162 may execute the prescription data review module 530a to, for example, cause the processor 162 to resolve third party review(s) (block 515d), resolve unauthorized prescription errors (block 520d), and/or follow a risk evaluation and mitigation strategy (REMS) procedure (block 525d).

The processor 162 may execute the predict return to stock module 545a to, for example, cause the processor 162 to predict whether a prescription will be returned to stock (block 530d). For example, the processor 162 may receive prescription data (block 505d) and/or patient health record data (block 510d), that is representative of a current prescription/patient, and may implement an associated predictive model based on the current prescription data and/or patient health record data to determine whether or not the patient will actually pick-up a medication and/or medical device associated with the prescription (block 535d).

Alternatively, or additionally, the processor 162 may receive prescription data (block 505d) and/or patient health record data (block 510d), that is representative of a current prescription/patient, and may implement an associated predictive model based on the current prescription data and/or patient health record data to determine a probability as to whether or not the patient will actually pick-up a medication and/or medical device associated with the prescription. The processor 162 may implement a plurality of predictive models (e.g., an extreme gradient boosting model, a neural network model, a decision tree model, a regression model, a stepwise regression model, a probability function model, etc.) and may base a final determination as to whether or not the patient will actually pick-up the medication and/or medical device based on outputs of a plurality of the predictive models (e.g., an average of the outputs, a weighted average of the outputs, a majority voting of the outputs, etc.).

In any event, if the processor 162 determines that the prescription will be picked up (or is more likely than not going to be picked up) (block 535d), the processor 162 may generate an indication to a pharmacist to fill the prescription under, for example, a standard operating procedure (SOP). If the processor 162 determines that the prescription will not be picked up (or is not likely to be picked up) (block 535*d*), the processor 162 may generate an indication to a pharmacist to hold the prescription (block 545*d*), and the processor 162 may execute the patient notification data generation module 550*a* to, for example, cause the processor 162 to generate patient notification data (block 550*d*). For example, the processor 162 may generate patient notification data (block 550*d*) based on a patient preference for receiving a notification via a text message, an email message, a tweet, a Facebook message, etc. The patient notification data may be representative of a notification to the patient that a prescription for the patient has been received by a pharmacy. The processor 162 may execute the patient notification data transmission module 555*a* to, for example, cause the processor 162 to transmit the patient notification data to a user device (block 550*d*).

The processor 162 may execute the patient response data receiving module 560*a* to, for example, cause the processor 162 to receive patient response data (blocks 555*d*, 560*d*, 565*d*). The patient response data may, for example, be generated/transmitted by a user device (e.g., user device 605*a* of FIG. 6A) as discussed with reference to FIGS. 6A and 6B. In any event, the patient response data may be indicative of the patient's intention to actually pick-up a medication and/or medical device associated with a prescription. The processor 162 may execute the return to stock decision module 565*a* to, for example, cause the processor 162 to determine whether or not a prescription should actually be filled (blocks 555*d*, 560*d*, 565*d*). For example, the processor 162 may generate an indication to a pharmacist to fill the prescription if the patient response is indicative that the patient will pick-up the prescription (block 555*d*). The processor 162 may generate an indication to a pharmacist to store the prescription on a patient file if the patient response is indicative that the patient will not pick-up the prescription (block 560*d*). The processor 162 may generate an indication to a pharmacist to fill the prescription if no patient response is received (block 565*d*). Alternatively, the processor 162 may generate an indication to a pharmacist to not fill the prescription if no patient response is received and the predictive model predicts that the prescription will not be picked up (block 535*d*) (block 565*d*).

Figure 6A:
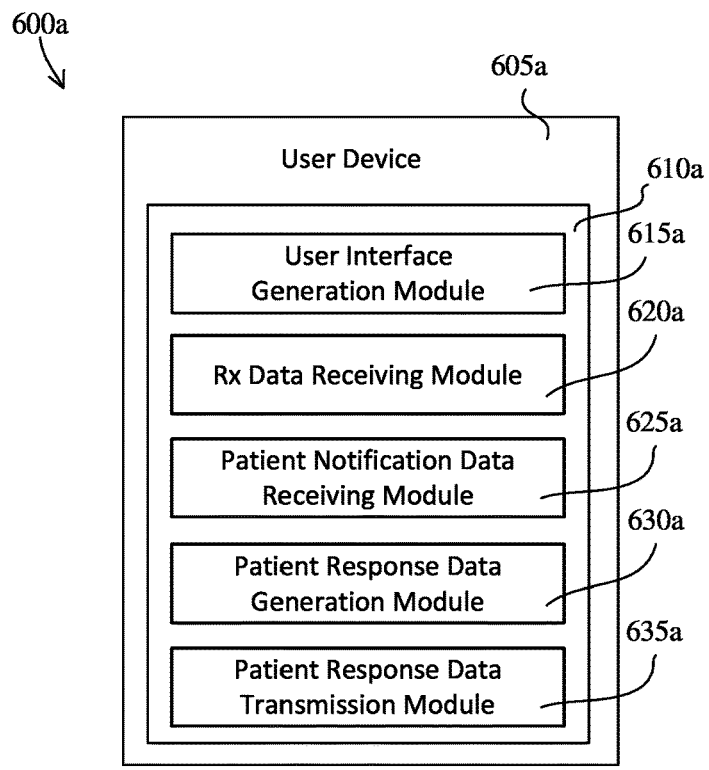
FIG. 6A depicts an example user device that notifies a patient that a pharmacy has received a prescription for the patient, and to receive a response from the patient.

With reference to FIG. 6A, a computer system for reducing return of prescriptions to stock 600*a* may include a user device 605*a*. The user device 605*a* may be similar to, for example, a workstation 128 of FIG. 1. In any event, the user device 605*a* may include a user interface generation module 615*a*, a prescription data receiving module 620*a*, a patient notification data receiving module 625*a*, a patient response data generation module 630*a*, and a patient response data transmission module 635*a*, for example, stored on a memory 610*a* as a set of computer-readable instructions. The memory 610*a* may be similar to, for example, the memory 160 of FIG. 1. Alternatively, any one of the modules 615*a*-635*a* may be configured as a dedicated hardware device (e.g., an application specific integrated circuit (ASIC), a logic circuit, an electrical circuit made up of discrete components, a field programmable gate array (FPGA), a hardware module, a sub-combination thereof, or a combination thereof, etc.). While not shown in FIG. 6A, the user device 605*a* may also include any one of, or all of, the modules 515*a*-565*a* of FIG. 5A.

Figure 6B:
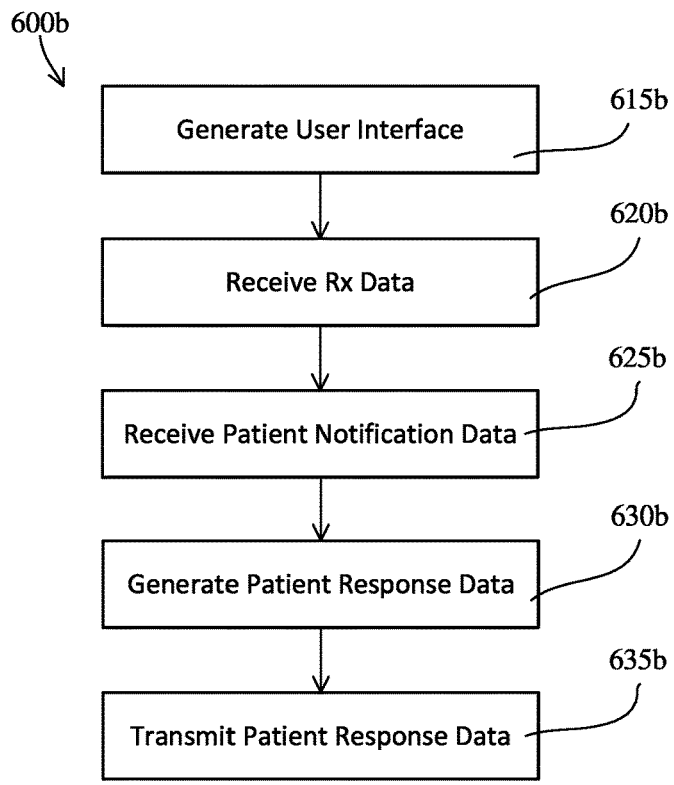
FIG. 6B depicts an example computer implemented method for implementing a user device to notify a patient that a pharmacy has received a prescription for the patient, and to receive a response from the patient.

Turning to FIG. 6B, a computer implemented method for receiving patient notification data, and generating and transmitting patient response data 600*b* may be implemented by, for example, the user device 605*a*. In particular, a processor (e.g., processor 128A of FIG. 1) may execute the user interface generation module 615*a* to, for example, cause the processor 128A to generate a patient prescription notification user interface (block 615*b*). For example, the processor 128A may generate a user interface display on a display device to enable a user to cause a computer device (e.g., a workstation 128 of FIG. 1, a smart-phone, a laptop computer, a personal digital assistant, etc.) to view a patient notification in regard to a prescription and to generate/transmit a user response. The user interface display may also enable a user to input user preferences (e.g., how/when to receive notifications, how/when to transmit responses, etc.).

The processor 128A may execute the prescription data receiving module 620*a* to, for example, cause the processor 128A to receive prescription data (block 620*b*). The processor 128A may execute the patient notification data receiving module 625*a* to, for example, cause the processor 128A to receive patient notification data from a remote device (e.g., remote device 505*a* of FIG. 5A). The patient notification data may be representative of a notification to the patient that a prescription for the patient has been received by a pharmacy.

The processor 128A may execute the patient response data generation module 630*a* to, for example, cause the processor 128A to generate patient response data (block 630*b*). The processor 128A may execute the patient response data transmission module 635*a* to, for example, cause the processor 128A to transmit the patient response data to a remote device 505*a* (block 635*b*). In any event, the patient response data may be indicative of the patient's intention to actually pick-up a medication and/or medical device associated with a prescription. Additionally, the processor 128A may generate patient response data (block 630*b*) based on a patient preference for receiving a notification via a text message, an email message, a tweet, a Facebook message, etc.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

ASPECTS OF THE INVENTION

Aspect 1—an apparatus for reducing return of prescriptions to stock may include a prescription data receiving module stored on a memory that, when executed by a processor, may cause the processor to receive prescription data. The prescription data may be representative of a prescription for a patient. The apparatus may also include a patient health record data receiving module stored on the memory that, when executed by the processor, may cause the processor to receive patient health record data. The prescription return to stock prediction data may be further based on the patient health record data. The apparatus may further include a return to stock prediction module stored on the memory that, when executed by the processor, may cause the processor to generate prescription return to stock prediction data based upon the prescription data, the patient health record data, and a predictive model. The prescription return to stock prediction data may be indicative of a probability of whether the prescription would be returned to stock.

Aspect 2—an apparatus for reducing return of prescriptions to stock may include a predictive model that is selected from the group: an extreme gradient boosting model, a neural network model, a decision tree model, a regression model, a stepwise regression model, or a probability function model.

Aspect 3—an apparatus for reducing return of prescriptions to stock may include a patient notification data generation module stored on the memory that, when executed by the processor, may cause the processor to generate patient notification data. The patient notification data may be representative of a notification to a patient that a pharmacy has received a prescription for the patient.

Aspect 4—an apparatus for reducing return of prescriptions to stock may include a prescription return to stock data receiving module stored on the memory that, when executed by the processor, may cause the processor to receive prescription return to stock data. The prescription return to stock data may be representative of at least one prescription that was known to have not been acquired by a patient. The apparatus may also include a predictive model generation module stored on the memory that, when executed by the processor, may cause the processor to generate a predictive model based on prescription data and the prescription return to stock data.

Aspect 5—an apparatus for reducing return of prescriptions to stock may include a prescription return to stock data receiving module stored on the memory that, when executed by the processor, may cause the processor to receive prescription return to stock data. The prescription return to stock data may be representative of at least one prescription that was known to have not been acquired by a patient. The apparatus may also include a predictive model generation module stored on the memory that, when executed by the processor, may cause the processor to generate a predictive model based on prescription data, the patient health record data, and the prescription return to stock data.

Aspect 6—an apparatus for reducing return of prescriptions to stock may include prescription data that is representative of at least one of: whether a prescription is an eRx, whether a prescription is a written Rx, whether a prescription is refill by autofill, whether a prescription is refill by IVR, whether a prescription is refill by internet, whether a prescription is associated with cash payment, whether a prescription is associated with an insurance rejection, whether a prescription is associated with an insurance rejection accept, what payment type a prescription is associated with, what medication type a prescription is associated with, whether a prescription is associated with a copay, number of days' supply associated with a prescription, whether a prescription is associated with an acute illness, whether a prescription is associated with a chronic illness, whether a prescription is associated with a brand, whether a prescription is associated with a generic, what drug manufacturer a prescription is associated with, whether a prescription is associated with a unique Rx count/day, whether a prescription is associated with a week day or weekend impact, a sub-combination thereof, or a combination thereof.

Aspect 7—an apparatus for reducing return of prescriptions to stock may include prescription data patient health record data that is representative of at least one of: a patient medication history, a most recent prescription fill date, a total prescription sold fill counts in the previous year, patient demographics, patient age, patient gender, patient median household income, provider demographics, provider age, provider gender, a prescription dispense as written (DAW) indication, a provider's specialty, or missing prescription value indicators.

Aspect 8—a computer-readable medium having computer-readable instructions stored thereon that, when executed by a processor, may cause the processor to generate a predictive model for predicting return of prescriptions to stock. The computer-readable medium may include a prescription data receiving module that, when executed by a processor, may cause the processor to receive prescription data. The prescription data may be representative of a prescription for a patient. The computer-readable medium may also include a prescription return to stock data receiving module that, when executed by the processor, may cause the processor to receive prescription return to stock data. The prescription return to stock data may be representative of at least one prescription that was known to have not been acquired by a patient. The computer-readable medium may further include a predictive model generation module that, when executed by the processor, may cause the processor to generate a predictive model based on the prescription data and the prescription return to stock data.

Aspect 9—a computer-readable medium may include a predictive model that is selected from the group: an extreme gradient boosting model, a neural network model, a decision tree model, a regression model, a stepwise regression model, or a probability function model.

Aspect 10—a computer-readable medium may include a patient health record data receiving module that, when executed by the processor, may cause the processor to receive patient health record data. A predictive model may be further based on the patient health record data.

Aspect 11—a computer-readable medium may include a patient notification data generation module that, when executed by the processor, may cause the processor to generate patient notification data. The patient notification data may be representative of a notification to a patient that a pharmacy has received a prescription for the patient.

Aspect 12—a computer-readable medium may include a patient notification data transmission module that, when executed by the processor, may cause the processor to transmit patient notification data to a user device.

Aspect 13—a computer-readable medium may include a patient response data generation module that, when executed by the processor, may cause the processor to generate patient response data. The patient response data may be representative of a patient response to the notification to the patient that the pharmacy has received the prescription for the patient. The patient response data may also be indicative of whether the patient intends to pick-up the prescription.

Aspect 14—a computer-readable medium may include a patient response data transmission module that, when executed by the processor, may cause the processor to transmit patient response data to a pharmacy device.

Aspect 15—a computer-implemented method to generate a predictive model for predicting return of prescriptions to stock may include receiving prescription data, at a processor, in response to the processor executing a prescription data receiving module. The prescription data may be representative of a prescription for a patient. The method may also include receiving prescription return to stock data, at the processor, in response to the processor executing a prescription return to stock data receiving module. The prescription return to stock data may be representative of at least one prescription that was known to have not been acquired by a patient. The method may further include generating, using the processor, a predictive model, based on the prescription data and the prescription return to stock data, in response to the processor executing a predictive model generation module.

Aspect 16—a method to generate a predictive model for predicting return of prescriptions to stock may include a predictive model that is selected from the group: an extreme gradient boosting model, a neural network model, a decision tree model, a regression model, a stepwise regression model, or a probability function model.

Aspect 17—a method to generate a predictive model for predicting return of prescriptions to stock may include receiving patient health record data, at the processor, in response to the processor executing a patient health record data receiving module. A predictive model may be based on the patient health record data.

Aspect 18—a method to generate a predictive model for predicting return of prescriptions to stock may include a predictive model that is based on at least one of: whether a prescription was subject to insurance reject, whether patient not insured (Cash Pay), whether a prescription is for MYLAN (Manufacturer), whether a prescription is to Auto-Fill (Refill channel), whether a prescription is being refilled too soon (Refill channel), whether a prescription requires a copay (log transformation), whether a prescription is for NASAL AGENTS-SYSTEMIC AND TOPICAL, whether a prescription is for ANTIVIRALS, whether a prescription is for ANTIHYPERLIPIDEMICS, whether a prescription is for ANALGESICS-ANTI-INFLAMMATORY, whether a prescription is for OPHTHALMIC AGENTS, whether a prescription is for DIURETICS, whether a prescription is for MUSCULOSKELETAL THERAPY AGENTS, whether a prescription is for DERMATOLOGICALS, whether a prescription is for ANTICONVULSANTS, whether a prescription is for VALAENT (Manufacturer), whether a prescription is for ANTIPSYCHOTICS/ANTIMANIC AGENTS, what is a Median Household Income for an associated patient is <30K (GIS proxy), whether a prescription is for Brand Medication, and whether a prescription is for ANTIASTHMATIC AND BRONCHODILATOR AGENTS.

Aspect 19—a method to generate a predictive model for predicting return of prescriptions to stock may include a predictive model that is based on at least one of: whether an associated prescription is subject to an insurance reject, whether patient not insured (Cash Pay), whether a prescription requires a copay (log transformation), what is a Median Household Income for an associated patient is <30K (GIS proxy), whether a prescription is for Brand Medication, whether a prescription is for MYLAN (Manufacturer), whether a prescription is for VALAENT (Manufacturer), whether a prescription is received via eRx, whether a prescription is for LAXATIVES, and whether a prescriber associated with a prescription is an ER doctor.

Aspect 20—a method to generate a predictive model for predicting return of prescriptions to stock may include a predictive model that is based on at least one of: whether an associated prescription is subject to an insurance reject, whether patient not insured (Cash Pay), whether a prescription requires a copay (log transformation), whether a prescription fill channel is missing, what is a Median Household Income for an associated patient is <30K (GIS proxy), whether a prescription is received via eRx, whether a prescription is for ANTIDIABETICS, whether a prescription is for Brand Medication, whether a prescription is for ANALGESICS—ANTI-INFLAMMATORY, whether a prescriber associated with a prescription is an ENT/Eye doctor, whether a prescriber associated with a prescription is a pediatrician, whether a prescription is for ANTIHYPERLIPIDEMICS, whether a prescription is for DERMATOLOGICALS, whether a prescriber associated with a prescription is an internal doctor, and what is a prescriptions count filled on the same index day.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. An apparatus for reducing return of prescriptions to stock, the apparatus comprising:
   one or more processors; and
   a non-transitory computer-readable medium having computer-readable instructions stored thereon that, when executed by the one or more processors, cause the one or more processors to:
   store pharmacy prescription information in a standardized pharmacy format about a prescription for a patient;
   receive, over a network in near real time, updated information from one or more users in a non-standardized electronic prescription format dependent on a hardware and software platform used by the one or more users, wherein an electronic prescription data is representative of the prescription for the patient;
   automatically receive patient health record data in response to the one or more processors receiving the electronic prescription data from the one or more users over the network;
   generate prescription return to stock prediction data based upon the electronic prescription data, the patient health record data, and a predictive model, wherein a prescription return to stock prediction data is indicative of a probability of whether the prescription for the patient would be returned to stock;
   convert, by the one or more processors, the electronic prescription data and the prescription return to stock prediction data to the pharmacy prescription information; and
   generate a pharmacy prescription in a standardized format based on an updated pharmacy prescription information.

2. The apparatus of claim 1, wherein the predictive model is selected from the group: an extreme gradient boosting model, a neural network model, a decision tree model, a regression model, a stepwise regression model, or a probability function model.

3. The apparatus of claim 1, wherein further execution of the instructions causes the one or more processors to:
generate patient notification data, wherein the patient notification data is representative of a notification to a patient that a pharmacy has received the prescription for the patient.

4. The apparatus of claim 1, wherein further execution of the instructions causes the one or more processors to:
receive prescription return to stock data, wherein the prescription return to stock data is representative of at least one prescription that was known to have not been acquired by the patient; and
generate the predictive model based on the electronic prescription data and the prescription return to stock data.

5. The apparatus of claim 1, wherein further execution of the instructions causes the one or more processors to:
receive prescription return to stock data, wherein the prescription return to stock data is representative of at least one prescription that was known to have not been acquired by the patient; and
generate the predictive model based on the electronic prescription data, the patient health record data, and the prescription return to stock data.

6. The apparatus of claim 1, wherein the electronic prescription data is representative of at least one of: whether a prescription is an eRx, whether a prescription is a written Rx, whether a prescription is a refill by autofill, whether a prescription is a refill by IVR, whether a prescription is a refill by internet, whether a prescription is associated with a cash payment, whether a prescription is associated with an insurance rejection, whether a prescription is associated with an insurance rejection accept, what payment type a prescription is associated with, what medication type a prescription is associated with, whether a prescription is associated with a copay, a number of days' supply associated with a prescription, whether a prescription is associated with an acute illness, whether a prescription is associated with a chronic illness, whether a prescription is associated with a brand, whether a prescription is associated with a generic, what drug manufacturer a prescription is associated with, whether a prescription is associated with a unique Rx count/day, whether a prescription is associated with a week day or weekend impact, a sub-combination thereof, or a combination thereof.

7. The apparatus of claim 1, wherein the patient health record data is representative of at least one of: a patient medication history, a most recent prescription fill date, a total prescription sold fill counts in a previous year, a patient demographics, a patient age, a patient gender, a patient median household income, a provider demographics, a provider age, a provider gender, a prescription dispense as written (DAW) indication, a provider's specialty, or a missing prescription value indicators.

8. A non-transitory computer-readable medium having computer-readable instructions stored thereon that, when executed by one or more processors, cause the one or more processors to:
store pharmacy prescription information in a standardized pharmacy format about a prescription of a patient;
receive, over a network in near real time, updated information from one or more users in a non-standardized electronic prescription format dependent on a hardware and software platform used by the one or more users, wherein an electronic prescription data is representative of the prescription for the patient;
automatically receive patient health record data in response to the one or more processors receiving the electronic prescription data from the one or more users over the network;
generate prescription return to stock prediction data based upon the electronic prescription data, the patient health record data, and a predictive model, wherein a prescription return to stock prediction data is indicative of a probability of whether the prescription for the patient would be returned to stock;
convert, by the one or more processors, the electronic prescription data and the prescription return to stock prediction data to the pharmacy prescription information; and
generate a pharmacy prescription in a standardized format based on an updated pharmacy prescription information.

9. The computer-readable medium of claim 8, wherein the predictive model is selected from the group: an extreme gradient boosting model, a neural network model, a decision tree model, a regression model, a stepwise regression model, or a probability function model.

10. The computer-readable medium of claim 8, further comprising:
a patient health record data receiving module that, when executed by the one or more processors, causes the one or more processors to receive the patient health record data, wherein the predictive model is further based on the patient health record data.

11. The computer-readable medium of claim 8, further comprising:
a patient notification data generation module that, when executed by the one or more processors, causes the one or more processors to generate patient notification data, wherein the patient notification data is representative of a notification to the patient that a pharmacy has received the prescription for the patient.

12. The computer-readable medium of claim 11, further comprising:
a patient notification data transmission module that, when executed by the one or more processors, causes the one or more processors to transmit patient notification data to a user device.

13. The computer-readable medium of claim 12, further comprising:
a patient response data generation module that, when executed by the one or more processors, causes the one or more processors to generate patient response data, wherein the patient response data is representative of a patient response to the notification to the patient that the pharmacy has received the prescription for the patient, and wherein the patient response data is indicative of whether the patient intends to pick-up the prescription.

14. The computer-readable medium of claim 13, further comprising:
a patient response data transmission module that, when executed by the one or more processors, causes the one or more processors to transmit the patient response data to a pharmacy device.

15. A computer-implemented method to generate a predictive model for predicting return of prescriptions to stock, the method comprising:
storing pharmacy prescription information in a standardized pharmacy format about a prescription of a patient;
receiving, over a network in near real time, updated information from one or more users in a non-standardized electronic prescription format dependent on a hardware and software platform used by the one or more users, wherein an electronic prescription data is representative of the prescription for the patient;

automatically receiving prescription return to stock data, at the one or more processors, in response to the one or more processors executing a prescription return to stock data receiving module and further in response to the one or more processors receiving the electronic prescription data, wherein the prescription return to stock data is representative of at least one prescription that was known to have not been acquired by the patient;

generating, using the one or more processors, a predictive model, based on prescription data and the prescription return to stock data, in response to the one or more processors executing a predictive model generation module;

converting, using the one or more processors, the electronic prescription data and prescription return to stock prediction data to the pharmacy prescription information; and generating a pharmacy prescription in a standardized format based on an updated pharmacy prescription information.

16. The method of claim 15, wherein the predictive model is selected from the group: an extreme gradient boosting model, a neural network model, a decision tree model, a regression model, a stepwise regression model, or a probability function model.

17. The method of claim 15, further comprising:

receiving patient health record data, at the one or more processors, in response to the one or more processors executing a patient health record data receiving module, wherein the predictive model is further based on patient health record data.

18. The method of claim 15, wherein the predictive model is based on at least one of: whether a prescription was subject to insurance reject, whether patient not insured (Cash Pay), whether a prescription is for MYLAN (Manufacturer), whether a prescription is to AutoFill (Refill channel), whether a prescription is being refilled too soon (Refill channel), whether a prescription requires a copay (log transformation), whether a prescription is for NASAL AGENTS-SYSTEMIC AND TOPICAL, whether a prescription is for ANTIVIRALS, whether a prescription is for ANTIHYPERLIPIDEMICS, whether a prescription is for ANALGESICS-ANTI-INFLAMMATORY, whether a prescription is for OPHTHALMIC AGENTS, whether a prescription is for DIURETICS, whether a prescription is for MUSCULO-SKELETAL THERAPY AGENTS, whether a prescription is for DERMATOLOGICALS, whether a prescription is for ANTICONVULSANTS, whether a prescription is for VALAENT (Manufacturer), whether a prescription is for ANTIPSYCHOTICS/ANTIMANIC AGENTS, what is a Median Household Income for an associated patient is <30K (GIS proxy), whether a prescription is for Brand Medication, and whether a prescription is for ANTIASTHMATIC AND BRONCHODILATOR AGENTS.

19. The method of claim 15, wherein the predictive model is based on at least one of: whether an associated prescription is subject to an insurance reject, whether patient not insured (Cash Pay), whether a prescription requires a copay (log transformation), what is a Median Household Income for an associated patient is <30K (GIS proxy), whether a prescription is for Brand Medication, whether a prescription is for MYLAN (Manufacturer), whether a prescription is for VALAENT (Manufacturer), whether a prescription is received via eRx, whether a prescription is for LAXATIVES, and whether a prescriber associated with a prescription is an ER doctor.

20. The method of claim 15, wherein the predictive model is based on at least one of: whether an associated prescription is subject to an insurance reject, whether patient not insured (Cash Pay), whether a prescription requires a copay (log transformation), whether a prescription fill channel is missing, what is a Median Household Income for an associated patient is <30K (GIS proxy), whether a prescription is received via eRx, whether a prescription is for ANTIDIABETICS, whether a prescription is for Brand Medication, whether a prescription is for ANALGESICS-ANTI-INFLAMMATORY, whether a prescriber associated with a prescription is an ENT/Eye doctor, whether a prescriber associated with a prescription is a pediatrician, whether a prescription is for ANTIHYPERLIPIDEMICS, whether a prescription is for DERMATOLOGICALS, whether a prescriber associated with a prescription is an internal doctor, and what is a prescriptions count filled on the same index day.

* * * * *